(12) United States Patent  
Sauvageau et al.

(10) Patent No.: US 11,795,190 B2  
(45) Date of Patent: Oct. 24, 2023

(54) D-GLYCERO-B-D-HEPTOSE 1-PHOSPHATE (HMP) CONJUGATES AND USE FOR TARGETED IMMUNE MODULATION

(71) Applicants: NATIONAL RESEARCH COUNCIL OF CANADA, Ottawa (CA); THE GOVERNING COUNCIL OF THE UNIVERSITY OF TORONTO, Toronto (CA)

(72) Inventors: Janelle Sauvageau, Ottawa (CA); Andrew Cox, Ottawa (CA); Xinyi Guo, North York (CA); Scott Gray-Owen, Oakvill (CA)

(73) Assignees: NATIONAL RESEARCH COUNCIL OF CANADA, Ottawa (CA); THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 319 days.

(21) Appl. No.: 16/957,173

(22) PCT Filed: Dec. 29, 2018

(86) PCT No.: PCT/CA2018/051652  
§ 371 (c)(1),  
(2) Date: Jun. 23, 2020

(87) PCT Pub. No.: WO2019/126873  
PCT Pub. Date: Jul. 4, 2019

(65) Prior Publication Data  
US 2020/0331949 A1    Oct. 22, 2020

Related U.S. Application Data

(60) Provisional application No. 62/611,640, filed on Dec. 29, 2017.

(51) Int. Cl.  
*C07H 11/04* (2006.01)  
*A61K 39/00* (2006.01)  
(Continued)

(52) U.S. Cl.  
CPC ............ *C07H 11/04* (2013.01); *A61K 39/002* (2013.01); *A61K 39/005* (2013.01);  
(Continued)

(58) Field of Classification Search  
None  
See application file for complete search history.

(56) References Cited

U.S. PATENT DOCUMENTS 5,798,343 A    8/1998   Zähringer et al.

FOREIGN PATENT DOCUMENTS

| WO | 2016054745 A1 | 4/2016 |
| WO | 2018205009 A1 | 11/2018 |
| WO | 2018205010 A1 | 11/2018 |

OTHER PUBLICATIONS

CAS Registry No. 408364-60-3, 1 page (first available 2002) (Year: 2002).*

(Continued)

*Primary Examiner* — Bong-Sook Baek

(57) ABSTRACT

Heptose-1-monophosphate-7-derivatives are modifiable immunomodulators that can be used to prepare clinically active conjugate compounds. Such conjugate compounds are useful in modulating an immune response in a subject.

12 Claims, 15 Drawing Sheets

Scheme 1:

(51) Int. Cl.
| | |
|---|---|
| A61K 39/002 | (2006.01) |
| A61K 39/005 | (2006.01) |
| A61K 39/008 | (2006.01) |
| A61K 39/015 | (2006.01) |
| A61K 39/02 | (2006.01) |
| A61K 39/108 | (2006.01) |
| A61K 39/112 | (2006.01) |
| A61K 39/08 | (2006.01) |
| A61K 39/085 | (2006.01) |
| A61K 39/09 | (2006.01) |
| A61K 39/095 | (2006.01) |
| A61K 39/118 | (2006.01) |
| A61K 39/125 | (2006.01) |
| A61K 39/145 | (2006.01) |
| A61K 39/15 | (2006.01) |
| A61K 39/155 | (2006.01) |
| A61K 39/205 | (2006.01) |
| A61K 39/215 | (2006.01) |
| A61K 39/23 | (2006.01) |
| A61K 39/235 | (2006.01) |
| A61K 39/39 | (2006.01) |
| A61K 45/06 | (2006.01) |
| C07H 13/00 | (2006.01) |
| A61K 47/54 | (2017.01) |

(52) U.S. Cl.
CPC ........ *A61K 39/008* (2013.01); *A61K 39/0011* (2013.01); *A61K 39/015* (2013.01); *A61K 39/0208* (2013.01); *A61K 39/0225* (2013.01); *A61K 39/0233* (2013.01); *A61K 39/0258* (2013.01); *A61K 39/0275* (2013.01); *A61K 39/0283* (2013.01); *A61K 39/0291* (2013.01); *A61K 39/08* (2013.01); *A61K 39/085* (2013.01); *A61K 39/092* (2013.01); *A61K 39/095* (2013.01); *A61K 39/099* (2013.01); *A61K 39/118* (2013.01); *A61K 39/125* (2013.01); *A61K 39/145* (2013.01); *A61K 39/15* (2013.01); *A61K 39/155* (2013.01); *A61K 39/205* (2013.01); *A61K 39/215* (2013.01); *A61K 39/23* (2013.01); *A61K 39/235* (2013.01); *A61K 39/39* (2013.01); *A61K 45/06* (2013.01); *A61K 47/549* (2017.08); *C07H 13/00* (2013.01)

(56) References Cited

OTHER PUBLICATIONS

Adekoya, I. A. et al. "D-Glycero-I3-D-Manno-Heptose 1-Phosphate and D-Glycerop-D-Manno-Heptose 1,7-Biphosphate Are Both Innate Immune Agonists." J. Immunol., 2018, doi:10.4049/jimmunol. 1801012.
Brimacombe, J. S. et al. "The synthesis of some seven-carbon sugars via the osmylation of olefinic sugars." Carbohydr. Res., 1986, 150, 35-51.
Brimacombe, J. S. et al. "Convenient syntheses of L-glycero-D-manno-heptose and D-glycero-omanno-heptose." Carbohydr. Res., 1986, 152, 329-334.
Crich, D. et al. "Eficient, diastereoselective chemical synthesis of beta-mannopyranosyl phosphoisoprenoid." Org. Lett., 2000, 2, 3941-3943.
Durka, M. et al. "Systematic synthesis of inhibitors of the two first enzymes of the bacterial heptose biosynthetic pathway: towards antivirulence molecules targeting lipopolysaccharide biosynthesis." Chem. Eur. J. 2011, 17, 11305-11313.
Gall A, et al. "TIFA signaling in gastric epithelial cells initiates the cag type 4 secretion system-dependent innate immune response to Helicobacter pylori infection." 2017. mBio 8:e01168-17.
Gaudet, R. G. et al. "Heptose Sounds the Alarm: Innate Sensing of a Bacterial Sugar Stimulates Immunity" PLOS Pathog. 2016, 12(9): e1005807.
Gaudet, R. G. et al. "Innate recognition of intracellular bacterial growth is driven by the TIFA-dependent cytosolic surveillance pathway". Cell Rep., 2017, 19, 1418-1430.
Gaudet, R. G. et al. "Cytosolic detection of the bacterial metabolite HBP activates TIFA-dependent innate immunity". Science, 2015, 384, 1251-1255.
Güzleck, H. et al. "A short synthesis of D-glycero-D-manno-heptose 7-phopshate". Carbohydr. Res., 2005, 340, 2808-2811.
Huang, H. et al. "Panoramic View of a Superfamily of Phosphatases Through Substrate Profiling." Proceedings of the National Academy of Sciences of the United States of America (2015), vol. 112, is.16, pp. EI974-EI983.
Hulyalkar, R.K. et al. "The synthesis of D-glycero-D-manno-heptose." Can. J. Chem., 1963, 41, 1490-1492.
Inuke, S. et al. "Chemical synthesis of D-glycero-D-manno-Heptose 1,7-Bisphosphate and Evaluation of its ability to modulate NF-kappa B activation." Org. Lett., 2017, DOI: 10.1021/acs.orglett. 7b01158.
Li, T. et al. "beta-stereoselective phosphorylations applied to synthesis of ADP- and polyprenyl-beta-mannopyranosides". Org. Lett., 2014, 16, 5628-5631.
Liang, L. et al. "Synthesis of D-glycero-D-manno-heptose 1,7-bisphosphate (HBP) featuring a p-stereoselective bis-phosphorylation". Tetrahedron Letters (2017), vol. 58, is. 37, 3631-3633.
Malott, R.J et al. "Neisseria gonorrhoeae-derived heptose elicits an innate immune response and drives HIV-1 expression." Proc. Natl. Acad. Sci., 2013, 110, 10234-10239.
Milivojevic, M. et al. "ALPK1 controls TIFA/TRAF6-dependent innate immunity against heptose-1,7-bisphosphate of gram-negative bacteria". PLOS Pathog. 2017, 13(2):e1006224.
Rosenfeld, D.A. et al. "Application of the cyanohydrin synthesis to D-altrose". J. Am. Chem. Soc., 1951, 73, 4907-4910.
Sabesan, S. et al. "Synthesis of glycosyl phosphates and azides". Carbohydr. Res. 1992, 223, 169-185.
Sauvageau, J. et al., "Alternate synthesis to D-glycero-beta-D-manno-heptose 1,7-biphosphate". Carbohydr. Res., 2017, 450, 38-43.
Wang, L. et al., Divergence of Biochemical Functionin the HAD Superfamily: D-glycero-D-manno-heptose-1,7-bisphosphatephosphatase (GmhB), Biochemistry(2010), vol. 49, is.6,p. 1072-1081.
Zamyatina, A et al. "Efficient chemical synthesis of both anomers of ADP L-glycero- and D-glycero-D-manno-heptopyranose". Carbohydr. Res., 2003, 338, 2571-2589.
Zhou, P. et al. "Alpha-kinase 1 is a cytosolic innate immune receptor for bacterial ADP-heptose". Nature, 2018, 561, 123-126.
Extended European Search Report issued for European Application No. 18896861.4, dated Oct. 26, 2021.

\* cited by examiner

Scheme 1:

Scheme 2:

$^1$H NMR, JS10 (600 MHz, D$_2$O)

$^1$H-$^{13}$C HSQC, JS10 (D$_2$O)

¹H NMR, 24 (500 MHz, D₂O) (JS11a)

¹³C NMR, 24 (150 MHz, CDCl₃) (JS11a)

$^1$H NMR, JS12a (600 MHz, D$_2$O)

$^{13}$C NMR, JS12a (150 MHz, CDCl$_3$)

$^1$H NMR, JS13a (500 MHz, D$_2$O)

LR-MS, JS13a

HPLC for JS13a $^1$H NMR, JS14a (400 MHz, D$_2$O)

$^{13}$C NMR, JS14a (100 MHz, CDCl$_3$)

$^1$H NMR, JS24a (600 MHz, $D_2O$)

$^1$H NMR, JS25a (600 MHz, $D_2O$)

D-GLYCERO-B-D-HEPTOSE 1-PHOSPHATE (HMP) CONJUGATES AND USE FOR TARGETED IMMUNE MODULATION

FIELD

The present invention relates generally to phosphorylated heptose compounds. More specifically, the present invention relates to use of heptopyranose phosphate and conjugates thereof in modulating, or targeting the modulation of, an immune response in a subject, to improve the specificity and effect of HMP and enhance protection.

BACKGROUND

The immune system provides protection against infectious agents, including bacteria, viruses, fungi, and parasites. A substantial number of medical conditions are associated with a compromised immune system and its associated increase in susceptibility to infectious agents. Thus, for example, patients undergoing surgery, radiation or chemotherapy, and those suffering from autoimmune diseases and diseases interfering with a normal metabolic immune response, such as HIV (AIDS), are all at a heightened risk of developing pathological conditions resulting from infection. While pharmaceuticals—antibiotics, such as ampicillin, tetracycline and quinolones, for example, in the case of bacterial infections—offer treatment options, resistance of the infectious agent to these pharmaceuticals is an increasingly significant concern.

Therefore, there is need for immune activating or modulating strategies to induce responses better able to prevent or combat infection. Furthermore, vaccines preventing or treating infection by many microbial organisms have been developed, however there is an ongoing need for additional vaccine formulations, as the immune stimulatory profile of known vaccine formulations is frequently suboptimal.

Vaccines have also been proposed to help the immune system target cancerous cells or tissues, however there is a need to improve the immune response so that it can more effectively combat the cancer. Finally, there is ongoing need to alter pathogenic immune responses, and particularly pathogenic inflammatory responses, to reduce disease symptoms and/or progression.

The ability to modulate the immune system of the host is becoming more and more critical as we strive to improve the immune response of individuals to generate a protective response. This is outlined for example in WO 2016/054745 entitled "Methods of modulating immune system responses." Understanding and exploiting potential new immunomodulation pathways are also critical to the development of new drugs.

Pathogen-associated molecular patterns (PAMPs; also known as microbial-associated molecular patterns, or MAMPs) are molecules produced by microbes that are specifically recognised and used as cues by the human immune system to generate innate and adaptive immune responses to keep foreign pathogens at bay. The ability to synthesise PAMPs will enable the specific modulation of the immune system to improve the immune response and generate protection.

Only a limited number of PAMPs have been identified, e.g. lipopolysaccharide (LPS), unmethylated CpG motifs within bacterial DNA, and flagellin. This limits the opportunity to investigate the immunomodulatory properties of these molecules. In most cases, PAMPs are difficult to synthesise completely or isolate at required and reproducible levels of purity, and thus precludes an opportunity to specifically address how these PAMPs interact with the immune system to exploit this relationship, when a pure, fully characterised supply of the PAMPs is unavailable.

Therefore, there is a need in the art to develop further PAMP molecules as treatment and prevention options against infections caused by infectious agents, cancerous cells and immune or inflammatory diseases.

SUMMARY

The inventors have identified phosphorylated heptose compounds (such as HMP) as PAMP-like molecules useful in modulating an immune response in a subject.

More specifically, in accordance with a first aspect of the invention, there is provided an HMP-linker corresponding to formula (I):

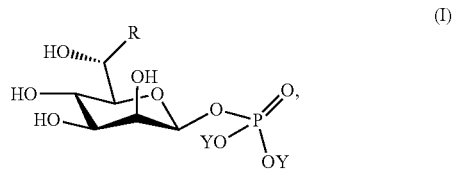

wherein group «R» is a linkage moiety adapted (or suitable) for conjugating with a functional molecule to form a conjugate, and Y is H or an appropriate atom for forming a salt thereof. Particularly, the conjugate is adapted (or capable) of modulating an immune response in a subject. More particularly, the conjugate is adapted (or capable) of targeting a modulation of an immune response in a subject.

Alternatively, the present invention provides an immunomodulatory compound comprising a molecule conjugated to a D-glycero-D-manno-heptopyranose 1β-phosphate (heptopyranose-1-monophosphate; HMP) moiety. Particularly, the molecule is a functional molecule, such as, for example, a drug, a cell surface antigen, a biological response modifier (BRM), a cell differentiation antigen specific binding partner or a marker. More particularly, the functional molecule is conjugated at position-7 of HMP or at position-2 of HMP, most particularly at position-7.

In accordance with a particular aspect, the invention provides a method to prepare an immunomodulator conjugate comprising the step of: conjugating a functional molecule with a compound of formula (I)

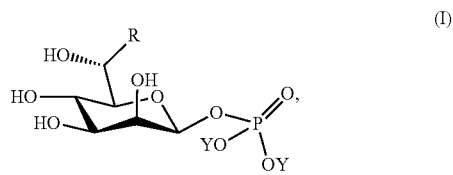

whereby the immunomodulator conjugate has immunomodulatory and/or targeting activity.

In accordance with an alternative aspect, the invention provides a conjugate compound of formula (II):

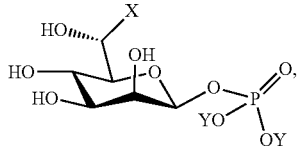

wherein X is a functional molecule and Y is H or an appropriate atom for forming a salt thereof, for use in targeting and/or modulating an immune response in a subject.

In accordance with a particular aspect, the use for modulating an immune response in a subject may comprise: a) improving the delivery of this HMP moiety into the cell. This could be achieved by linking the HMP moiety to a lipid or fatty acid or other molecule that would improve the permeability of HMP across cell membranes; b) treating an HIV infection by stimulating HIV latently-infected cells to start producing virus, and killing the produced virus; whereby the HMP-anti-HIV conjugate eradicates the latent viral pool and treats the HIV infection; or c)

In accordance with an alternative aspect, the invention provides a use of an effective amount of a compound of formula (II) as defined herein, for targeting and/or modulating an immune response in a subject.

Alternatively, the invention provides a use of a conjugate-compound of formula (II) for the manufacture of a medicament for targeting and/or modulating an immune response in a subject.

In accordance with an alternative aspect, the invention provides a method for modulating an immune response in a subject, comprising administering an effective amount of the conjugate-compound of formula (II) as defined herein.

In accordance with an alternative aspect, the invention provides a method for improving the delivery of this HMP moiety into the cell. This could be achieved by linking the HMP moiety to a lipid or fatty acid or other molecule that would improve the permeability of HMP across cell membranes In accordance with a particular aspect, there is provided a method for the treatment of HIV comprising the steps of: administering an HMP-derivative conjugated to an anti-HIV molecule, wherein the HMP moiety stimulates HIV latently-infected cells to start producing virus, and wherein the anti-HIV molecule kills the produced virus; whereby the HMP-anti-HIV conjugate eradicates the latent viral pool and treats the HIV infection.

In accordance with a particular aspect, there is provided a method for treating latent HIV infection comprising the steps of: administering an HMP-derivative conjugated to an HIV-reservoir cell-specific targeting molecule to a subject, and treating said subject with an anti-HIV drug, wherein the HMP moiety stimulates HIV latently-infected cells to produce virus, and the anti-HIV drug kills the produced virus; whereby the method eradicates the latent HIV viral pool.

In accordance with a further aspect, the invention provides a method for synthesizing a compound of formula (II) comprising the steps of Scheme 1 (FIG. 1A):

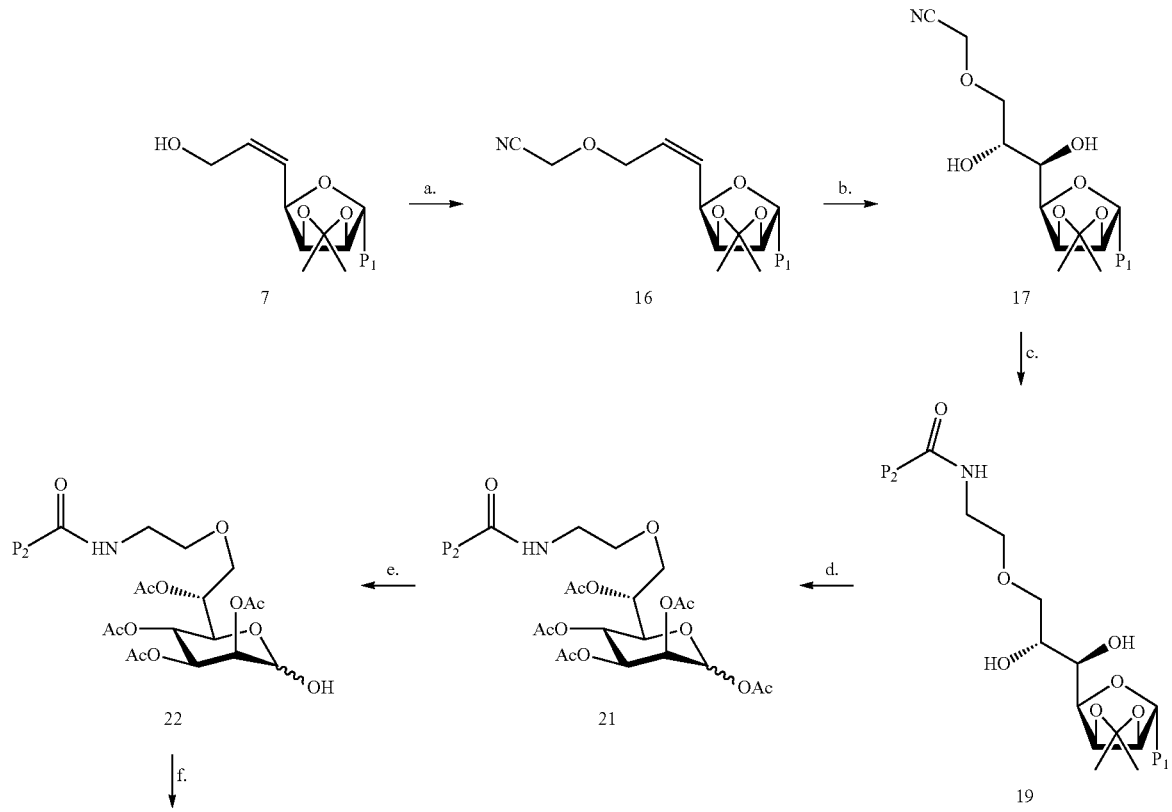

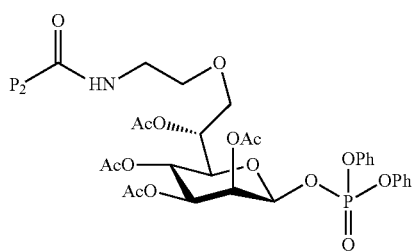

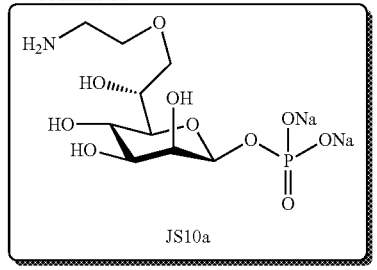

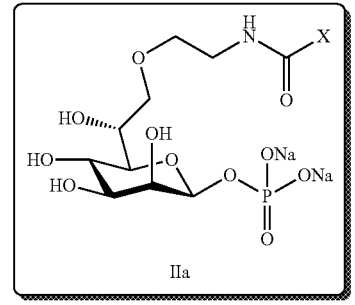

a. protection of hydroxy group of compound 7;
b. hydroxylation of double bond of compound 16;
c. reduction of compound 17;
d. protection with protecting group, cleavage of acetonide and protecting group and acetylation gave acetylated compound 21;
e. deprotection of anomeric acetyl;
f. phosphorylation;
g. deprotection to form JS10a; and i or
j. conjugation to a functional molecule X-activated ester to yield a molecule (IIa) which is a particular embodiment of the compound of formula (II).

Other objects, advantages and features of the present invention will become more apparent upon reading of the following non-restrictive description of specific embodiments thereof, given by way of example only with reference to the accompanying drawings.

DESCRIPTION

Abbreviations

Figure 1A:
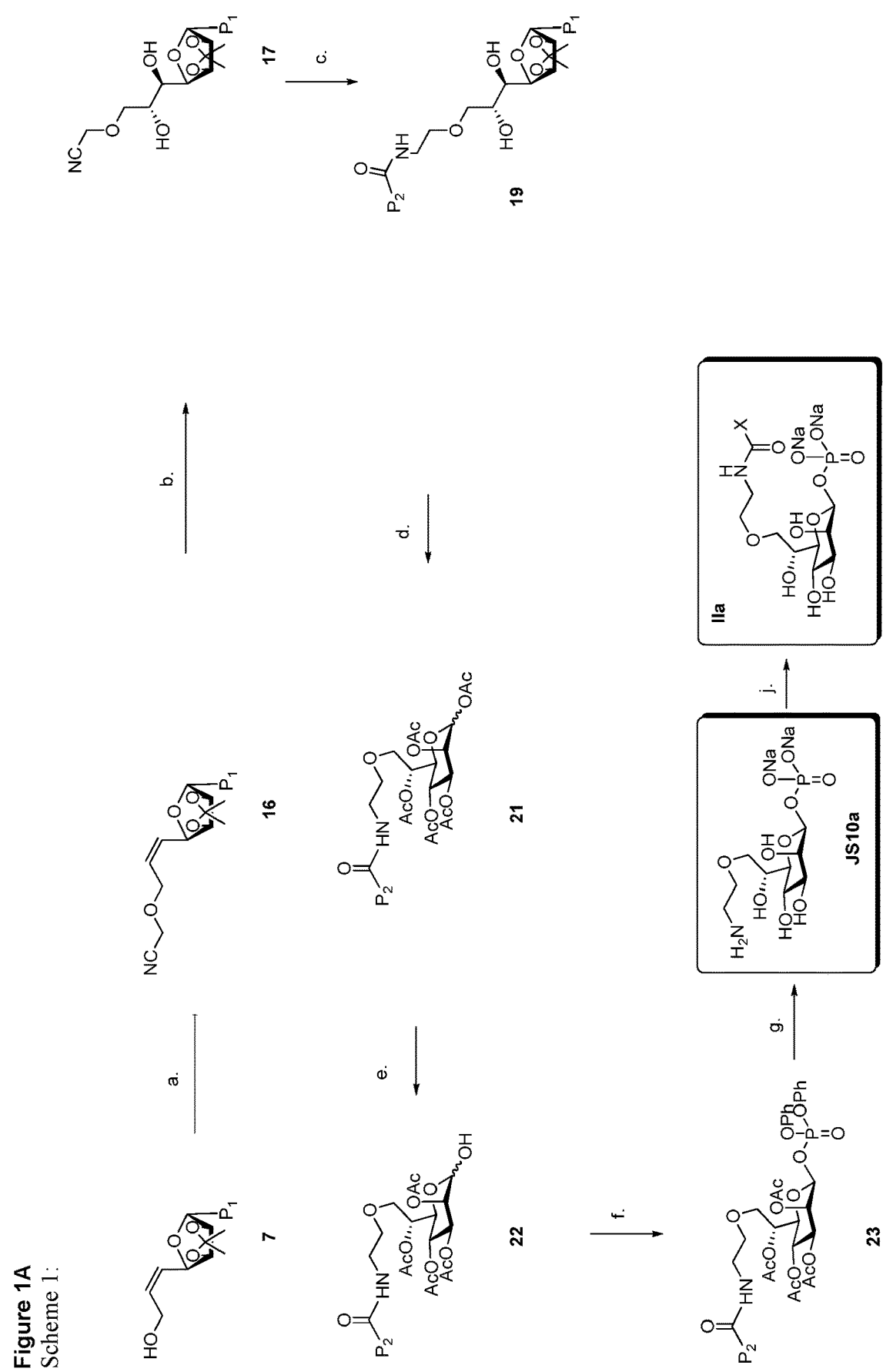
FIG. 1A. Reaction scheme 1 for the general synthesis of derivative linkers of HMP-β.

CRM: cross-reacting material (a genetic mutant of diphtheria toxin); HBP: heptose-1,7-biphosphate or D-glycero-D-manno-heptopyranose-1,7-β-phosphate; HMP-β: D-glycero-D-manno-heptopyranose-1β-phosphate (also named heptose-1-monophosphate or JS7); PAMP: pathogen associated molecular pattern; GFP: green fluorescent protein; Sup: supernatant; WT: wild type; TIFA: tumor necrosis factor receptor-associated factor (TRAF)-interacting protein with forkhead-associated domain; TIFA KO: TIFA protein expression knockout.

Definitions

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the terms "$C_{1-6}$" (or more generally "$C_{x-y}$") means a chain containing from 1 to 6 carbon atoms (or more generally x to y carbon atoms), being saturated or unsaturated, linear or branched, as permitted by the laws of organic chemistry, well understood by the person skilled in the art.

As used herein, the term "phosphorylated heptose compound" refers to a monosaccharide with seven carbon atoms, wherein at least one hydroxyl group is replaced by a group comprising a phosphorus atom. For example, the term "mono-phosphorylated heptose compound" refers a monosaccharide with seven carbon atoms, wherein one hydroxyl group is replaced by a group comprising a phosphorus atom. The term also refers to a derivative or an analogue of such compound.

As used herein, the term "label", "marker" or "tag" refer to any molecule used in such a way as to attach a functional or diagnostic or other moiety to the molecule, such as but not limited to fluorescent tags, affinity tags, transfer factor, plasmids or lipids, in such a way that the bioactivity can be for example but not limited to followed, targeted, directed or modified or otherwise guided, analyzed or assessed.

As used herein, the term "modulate" in connection with an immune or inflammatory response refers to a qualitative or quantitative alteration in the immune or inflammatory response in a subject.

As used herein, the term "vaccine" or "vaccine composition" refers to a pharmaceutical composition containing an immunogen. The composition may be used for modulating an immune response in a subject. The term also refers to subunit vaccines, i.e., vaccine compositions containing immunogens which are separate and discrete from a whole organism with which the immunogen is associated in nature.

As used herein, the term "effective amount" refers to the amount of a compound medicinal molecule or reaction product sufficient to cure, alleviate or partially arrest the clinical manifestations of a given disease and its complications in a therapeutic intervention comprising the administration of said compound or reaction product. An effective amount for each purpose will depend on the severity of the disease or injury as well as the weight and general state of the subject.

As used herein, the term "functional molecule" refers to a molecule that is administrable to a mammal for modulating or labeling a least one physiological parameter, marker or target in a cell, organ, biological system, organism or mammal.

In general, the methods of the present disclosure may be used to therapeutically or prophylactically treat any subjects for which increased activation of the immune system or an altered immune response would be beneficial. This includes, but is not restricted to a subject suffering from a condition which deleteriously affects the immune system, including any subjects at a heightened risk of infection or actually infected, for example due to surgery or imminent surgery, injury, illness, radiation or chemotherapy, and any subjects suffering from autoimmune diseases, inflammatory disorders, cancers, and diseases which cause the normal metabolic immune response to be compromised, such as HIV (AIDS).

As used herein the terms "prevention" and "preventing" mean the management and care of a subject for the purpose of preventing the occurrence of a condition, such as a disease or disorder. The composition may be used for inducing or enhancing an immune response against a potential pathogen in a subject for blocking infection, delaying onset or decreasing transmission. The subject to be treated is preferably a mammal, in particular a human being.

As used herein the terms "treatment" and "treating" mean the management and care of a subject for the purpose of combating a condition, such as a disease or disorder. The term is intended to include the full spectrum of treatments for a given condition from which the patient is suffering, such administration of the active compounds to alleviate the symptoms or complications, to delay the progression of the condition, and/or to cure or eliminate the condition. The subject to be treated is preferably a mammal, in particular a human being.

As used herein, the term "subject" is understood as being any mammal including a human being treated with a compound of the invention.

Before the present invention is further described, it is to be understood that the invention is not limited to the particular embodiments described below, as variations of these embodiments may be made and still fall within the scope of the appended claims. It is also to be understood that the terminology employed is for the purpose of describing particular embodiments and is not intended to be limiting. Instead, the scope of the present invention will be established by the appended claims.

DETAILED DESCRIPTION OF PARTICULAR EMBODIMENTS

The technology is directed to β-D-heptose-1-phosphate (HMP)-linker derivatives and molecule conjugates of β-D-heptose-1-phosphate (HMP) for modulating an immune response in a subject. Observation of biological activity of the HMP molecule was not at all expected based on prior art. Indeed, previous studies had indicated that loss of the 7-phosphate from the 1,7-biphosphate molecule eliminated activity. This observation of activity of the 1-phosphate (HMP) linker provides a unique opportunity to fully understand the scope of the immunomodulatory possibilities and provide a reproducible methodology that could provide milligram to gram quantities of a potentially valuable biological molecule. The proof of activity of the HMP creates two major advantages.

Firstly, the synthesis of the HMP is significantly simpler and likely more commercially realisable than that of the HBP. Secondly, this creates the potential opportunity to modify the 7-position of the HMP to link this immunomodulator to a huge variety of functional molecules whose processing and activity may be controlled and directed by conjugation to this PAMP-like molecule.

Experiments involved replacing the terminal OH group of the glycerol moiety in HMP with another chemical entity to introduce a linkage moiety, were carried out to facilitate the production of novel immunomodulatory compounds with improved protection and efficiency.

The inventors have identified phosphorylated heptose-derivatives useful for conjugating with a functional molecule and modulating their immunomodulatory activities thereof. These conjugates may be useful in modulating (i.e. enhancing or decreasing) an immune response in a subject or labeling the molecule in such a way that it may be followed, targeted, directed or modified or otherwise guided.

HMP-Linker

In accordance with a particular embodiment of the present invention, there is provided an HMP-linker compound of formula (I) or (Ia):

(I)

(Ia)

wherein R is a linkage moiety for conjugating with a functional molecule. Particularly, the resulting HMP-conjugate is capable of modulating an immune response in a subject.

In accordance with a particular embodiment, R is selected from the group consisting of: —C(O)OH, —C(O)H, —C$_{0-6}$alkyl-C(O)—C$_{1-6}$ alkyl, —C$_{0-6}$alkyl-N$_3$, —C$_{1-6}$ alkyl, —C$_{0-6}$alkyl —O—C$_{1-6}$ alkyl, —C$_{0-6}$alkyl-aryl, —C$_{0-6}$alkyl-O-aryl, —C$_{0-6}$alkyl-C$_{2-6}$-allyl groups, and —C$_{0-6}$alkyl-O—C$_{2-6}$-allyl, wherein said —C$_{0-6}$alkyl-C(O)—C$_{1-6}$alkyl, —C$_{1-6}$alkyl, C$_{0-6}$alkyl-O—C$_{1-6}$ alkoxy, -aryl, C$_{0-6}$alkyl-O-aryl, C$_{0-6}$alkyl-C$_{2-6}$-allyl groups, and C$_{0-6}$alkyl-O—C$_{2-6}$-allyl is optionally substituted with a: amino, acyloxy, alkoxy, carboxyl, carbalkoxyl, hydroxy, trifluoromethyl, cyano, nitro, acyl, or a halo group;

or R is selected from the group consisting of: —C$_{1-6}$ alkyl-OPO$_3$C(O)—C$_{1-6}$ alkyl, —C$_{1-6}$ alkyl-OPO$_3$C$_{1-6}$ alkyl, —C$_{1-6}$ alkyl-OPO$_3$—C$_{1-6}$—O-alkoxy, —C$_{1-6}$ alkyl-OPO$_3$-aryl, —C$_{1-6}$ alkyl-OPO$_3$—C$_{2-6}$-allyl, wherein said —C$_{1-6}$ alkyl-OPO$_3$C(O)—C$_{1-6}$alkyl, —C$_{1-6}$ alkyl-OPO$_3$C$_{1-6}$ alkyl, —C$_{1-6}$ alkyl-OPO$_3$—C$_{1-6}$—O-alkoxy, —C$_{1-6}$ alkyl-OPO$_3$-aryl, —C$_{1-6}$ alkyl-OPO$_3$—C$_{2-6}$-allyl group is optionally substituted with a: amino, acyloxy, alkoxy, carboxyl, carbalkoxyl, hydroxy, trifluoromethyl, cyano, nitro, acyl, or a halo group;

or a salt thereof.

In accordance with a particular embodiment, R is selected from the group consisting of: —C(O)OH, —C(O)H, —C(O)—C$_{1-6}$ alkyl, —N$_3$, —C$_{1-6}$ alkyl, —O—C$_{1-6}$ alkyl, -aryl, —O-aryl, —C$_{2-6}$-allyl groups, and —O—C$_{2-6}$-allyl, wherein said —C(O)—C$_{1-6}$ alkyl, —C$_{1-6}$ alkyl, —O—C$_{1-6}$ alkoxy, -aryl, —O-aryl, —C$_{2-6}$-allyl groups, and —O—C$_{2-6}$-allyl is optionally substituted with: amino, acyloxy, alkoxy, carboxyl, carbalkoxyl, hydroxy, trifluoromethyl, cyano, nitro, acyl, or a halo group;

or R is selected from the group consisting of: CH$_2$OPO$_3$C(O)—C$_{1-6}$alkyl, CH$_2$OPO$_3$C$_{1-6}$ alkyl, CH$_2$OPO$_3$—C$_{1-6}$—O alkoxy, CH$_2$OPO$_3$-aryl, CH$_2$OPO$_3$—C$_{2-6}$-allyl, wherein said CH$_2$OPO$_3$C(O)—C$_{1-6}$ alkyl, CH$_2$OPO$_3$C$_{1-6}$ alkyl, CH$_2$OPO$_3$—C$_{1-6}$—O alkoxy, CH$_2$OPO$_3$-aryl, CH$_2$OPO$_3$—C$_{2-6}$-allyl group is optionally substituted with a: amino, acyloxy, alkoxy, carboxyl, carbalkoxyl, hydroxy, trifluoromethyl, cyano, nitro, acyl, or a halo group; or a salt thereof.

In accordance with a particular embodiment, R is selected from the group consisting of: —C$_{1-6}$alkyl, —C(O)OH, —C(O)H, —C(O)—C$_{1-6}$ alkyl, —C$_{0-6}$alkyl-O—C$_{1-6}$ alkyl, —C$_{0-6}$alkyl-C$_{2-6}$-allyl groups, and —O—C$_{2-6}$-allyl, wherein each of said —C$_{1-6}$alkyl, —C(O)—C$_{1-6}$alkyl, —C$_{0-6}$alkyl-O—C$_{1-6}$ alkyl, —C$_{0-6}$alkyl-C$_{2-6}$-allyl, and —C$_{0-6}$alkyl-O—C$_{2-6}$-allyl group is optionally substituted with a: amino, alkoxy, hydroxy, carboxy or nitro group;

or R is selected from the group consisting of: CH$_2$OPO$_3$C(O)—C$_{1-6}$alkyl, CH$_2$OPO$_3$C$_{1-6}$ alkyl, CH$_2$OPO$_3$—C$_{1-6}$—O alkoxy, CH$_2$OPO$_3$-aryl, CH$_2$OPO$_3$—C$_{2-6}$-allyl, wherein each of said CH$_2$OPO$_3$C(O)—C$_{1-6}$ alkyl, CH$_2$OPO$_3$C$_{1-6}$ alkyl, CH$_2$OPO$_3$—C$_{1-6}$—O alkoxy, CH$_2$OPO$_3$-aryl, CH$_2$OPO$_3$—C$_{2-6}$-allyl group is optionally substituted with a: amino, alkoxy, hydroxy, or nitro group; or a salt thereof.

In accordance with a particular embodiment of the present invention, there is provided an HMP-linker compound of formula (Ia):

(Ia)

wherein R is a linkage moiety for conjugating with a functional molecule. Particularly, the resulting HMP-conjugate is capable of modulating an immune response in a subject.

In accordance with a particular embodiment, R is selected from the group consisting of: —C(O)—C$_{1-6}$ alkyl, —N$_3$, —C$_{1-6}$ alkyl, —O—C$_{1-6}$ alkyl, -aryl, —O-aryl, —C$_{2-6}$-allyl groups, and —O—C$_{2-6}$-allyl, wherein each of said —C(O)—C$_{1-6}$ alkyl, —C$_{1-6}$ alkyl, —O—C$_{1-6}$ alkoxy, -aryl, —O-aryl, —C$_{2-6}$-allyl, and —O—C$_{2-6}$-allyl groups is optionally substituted with a: amino, alkoxy, hydroxy, or nitro group; or R is selected from the group consisting of: CH$_2$OPO$_3$C(O)—C$_{1-6}$ alkyl, CH$_2$OPO$_3$C$_{1-6}$ alkyl, CH$_2$OPO$_3$—C$_{1-6}$—O alkoxy, CH$_2$OPO$_3$-aryl, CH$_2$PO$_3$—C$_{2-6}$-allyl, wherein each of said CH$_2$OPO$_3$C(O)—C$_{1-6}$ alkyl, CH$_2$OPO$_3$C$_{1-6}$ alkyl, CH$_2$OPO$_3$—C$_{1-6}$—O alkoxy, CH$_2$OPO$_3$-aryl, CH$_2$OPO$_3$—C$_{2-6}$-allyl group is optionally substituted with a: amino, alkoxy, hydroxy, or nitro group.

In accordance with a particular embodiment, the HMP-linker of formula (I) or (Ia) is substituted with an "R" group that may be selected from the group consisting of: —C(O)OH, —C(O)H, —C(O)C$_{1-6}$ alkyl, —CH$_2$N$_3$, —CH$_2$OC$_{1-6}$ alkyl, —CH$_2$Oaryl, and —CH$_2$OC$_{2-6}$-allyl groups, wherein said —C(O)C$_{1-6}$ alkyl, —CH$_2$OC—$_{1-6}$ alkyl, —CH$_2$Oaryl, and —CH$_2$OC$_{2-6}$-allyl group is optionally substituted with a: amino, acyloxy, alkoxy, carboxyl, carbalkoxyl, hydroxy, trifluoromethyl, cyano, nitro, acyl, or a halo group; or a salt thereof. More particularly, the group R is: CH$_2$—CH$_2$CH$_2$—NH$_2$; —C(O)OH, —C(O)H, —C(O)NH$_2$ or —CH$_2$N$_3$ or CH$_2$NH$_2$.

Additionally, it is possible to modify HMP via a phosphate residue, wherein R is CH$_2$OPO$_3$C(O)—C$_{1-6}$ alkyl, CH$_2$OPO$_3$C$_{1-6}$ alkyl, CH$_2$OPO$_3$—C$_{1-6}$—O alkoxy, CH$_2$OPO$_3$-aryl, CH$_2$OPO$_3$—C$_{2-6}$-allyl. wherein said CH$_2$OPO$_3$C(O)—C$_{1-6}$ alkyl, CH$_2$OPO$_3$C$_{1-6}$ alkyl, CH$_2$OPO$_3$—C$_{1-6}$—O alkoxy, CH$_2$OPO$_3$-aryl, CH$_2$OPO$_3$—C$_{2-6}$-allyl groups, is optionally substituted with a: amino, acyloxy, alkoxy, carboxyl, carbalkoxyl (alkoxycarbonyl), hydroxy, trifluoromethyl, cyano, nitro, acyl, or a halo group; or a salt thereof.

More particularly, R is selected from the group consisting of: C$_{1-6}$alkyl-NH$_2$; —C$_{0-6}$ alkyl-C—O—C$_{0-6}$ alkyl-NH$_2$, —C(O)OH, —C(O)H, —C$_{0-6}$ alkyl-C(O)C$_{0-6}$ alkyl-NH$_2$, C$_{0-6}$alkyl-N$_3$. Most particularly, R is selected from the group consisting of: CH$_2$—NH$_2$; —C(O)OH, —C(O)H, —C(O)NH$_2$ and —N$_3$.

More particularly, R is selected from the group consisting of: CH$_2$—NH$_2$; —C(O)OH, —C(O)H, —C(O)NH$_2$ and —N$_3$.

According to a particular embodiment, the HMP-linker may be chosen from:

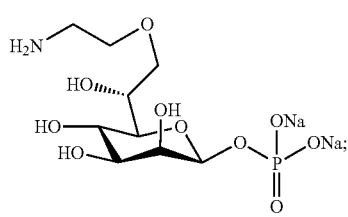
JS10a

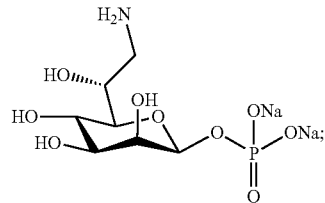
JS15

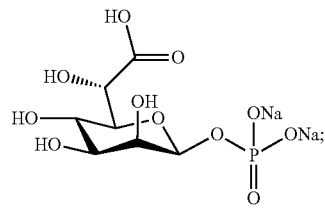
JS16

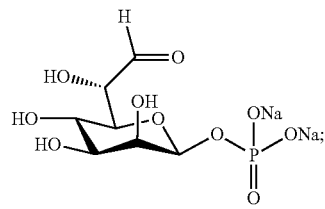
JS17

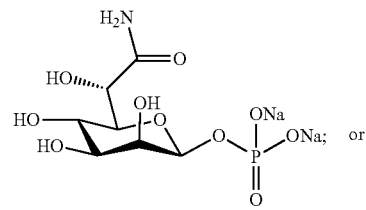
JS18

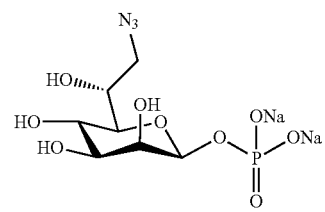
JS19

Conjugates

These conjugate-compounds (or conjugates) can now be targeted to the unique arm of the immune system that processes HMP/HBP, thus potentially enhancing the immunological impact of the conjugated functional molecule.

In accordance with a particular aspect of the invention, there is provided a compound comprising a functional molecule conjugated to a D-glycero-D-manno-heptopyranose 1β-phosphate (heptopyranose-1-monophosphate; HMP) moiety. In a particular embodiment, the functional molecule is conjugated at position-7 of HMP, or -2 of HMP. Particularly, the functional molecule is conjugated at position-7 of HMP.

In accordance with a particular embodiment, the invention provides a conjugate compound of formula (II) as defined herein, for use in targeting and/or modulating an immune response in a subject.

According to a particular embodiment, the conjugate-compound is defined by formula (IIa):

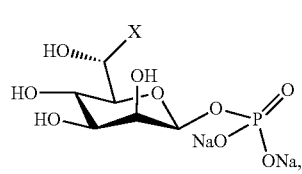

(IIa)

wherein X is a conjugated functional molecule.

Molecules for Conjugating to HMP-Linker

In accordance with a particular embodiment, the HMP-linker is conjugated to a functional molecule for modulating a host's immune response to this functional molecule. Particularly, the functional molecule is a protein (e.g. carrier proteins such as: CRM, protein D, or TT), polypeptide (e.g. Ova-specific peptide: CGGSIINFEKLTEWTSSNVMEER (SEQ ID No.1)), an antibody, a lipid (e.g. glycerolipid), a fatty acid (e.g. stearic acid or palmitic acid), a carbohydrate, a drug, a fluorescent tag, an affinity tag or a transfer factor molecule. Particularly, the functional molecule is an antigen, a biological response modifier (BRM, such as a hormone, immunogen, antibody, etc.) or a marker.

Alternatively, the functional molecule is a drug such as, for example, an anti-HIV drug including, but not limited to: Nucleoside/Nucleotide reverse transcriptase inhibitors (NRTI), such as for example, abacavir (ziagen), efavirenz/emtriacitabine/tenofovir disoproxil fumarate (atripla), lamivudine/zidovudine (combivir), emtriacitabine/rilpivirine/tenofovir disoproxil fumarate (complera), emtricitabine (emtriva), lamivudine (Epivir), abacavir/lamivudine (Epzicom), zidovudine (Retrovir), abacavir/lamivudine/zidovudine (Trizivir), emtricitabine/tenofovire disoproxil fumarate (Truvada), didanosine (Videx), didanosine extended release (Videx EC), tenofovir disoproxil fumarate (Viread), stavudine (Zerit); Multiclass combination drugs: such as efavirenz/emtricitabine/tenofovir disoproxil fumarate (Atripla), emtricitabine/rilpivirine/tenofovir disoproxil fumarate (Complera), elvitegravir/cobicistat/emtricitabine/tenofovir disoproxil fumarate (Stribild), abacavir/dolutegravir/lamivudine (Triumeq); Non-nucleoside reverse transcriptase inhibitors (NNRTIs), such as, but not limited to: rilpivirine (Edurant), etravirine (Intelence), delavirdine mesylate (Rescriptor), efavirenz (Sustiva), nevirapine (Viramune), nevirapine extended-release (Viramune XR); Protease inhibitors (PI) suhc as, but not limited to: tipranavir (Aptivus), indinavir (Crixivan), atazanavir/cobicistat (Evotaz), saquinavir (Invirase), lopinavir/ritonavir (Kaletra), fosamprenavir (Lexiva), ritonavir (Norvir), darunavir/cobicistat (Prezcobix), darunavir (Prezista), atazanavir (Reyataz), nelfinavir (Viracept); Entry inhibitors (including fusion inhibitors) such as, but not limited to: enfuvirtide (Fuzeon); Integrase inhibitors, such as, but not limited to: raltegravir (Isentress), dolutegravir (Tivicay), elvitegravir (Vitekta); Chemokine co-receptor antagonists (CCR5 antagonists), such as, for example: maraviroc (Selzentry); Cytochrome P4503A (CYP3A) inhibitors, such as, but not limited to: cobicistat (Tybost).

Some anti-HCV drugs, such as, for example: protease inhibitors (PI) approved for hepatitis C only are sometimes prescribed by doctors for HIV: simeprevir (Olysio), boceprevir (Victrelis), ombitasvir/paritaprevir/ritonavir/dasabuvir (Viekira Pak).

The functional molecule that could be linked to HMP may include anti-cancer drugs, such as, but not limited to: Abiraterone, Alemtuzumab, Anastrozole, Aprepitant, Arsenic trioxide, Atezolizumab, Azacitidine, Bevacizumab, Bleomycin, Bortezomib, Cabazitaxel, Capecitabine, Carboplatin, Cetuximab, Chemotherapy drug combinations, Cisplatin, Crizotinib, Cyclophosphamide, Cytarabine, Denosumab, Docetaxel, Doxorubicin, Eribulin, Erlotinib, Etoposide, Everolimus, Exemestane, Filgrastim, Fluorouracil, Fulvestrant, Gemcitabine, HPV Vaccine, Imatinib, Imiquimod, Ipilimumab, Ixabepilone, Lapatinib, Lenalidomide, Letrozole, Leuprolide, Mesna, Methotrexate, Nivolumab, Oxaliplatin, Paclitaxel, Palonosetron, Pembrolizumab, Pemetrexed, Prednisone, Radium-223, Rituximab, Sipuleucel-T, Sorafenib, Sunitinib, Talc Intrapleural, Tamoxifen, Temozolomide, Temsirolimus, Thalidomide, Trastuzumab, Vinorelbine, or Zoledronic acid.

Alternatively, the functional molecule is an antigen, more particularly a molecule that targets a cell differentiation antigen, such as a-specific binding partner for targeting the HMP moiety to a particular type of cells, be it cancer cells, immune cells, or cells of any particular organ or location in the body.

Antigen for Targeting Specific Cells

Particularly, when the conjugated functional molecule is a molecule that targets a cell differentiation antigen, such as a specific binding partner, this molecule may be used as a "magic bullet" to target the immunomodulatory HMP moiety to a particular type of cells, such as, for example, HIV reservoir cells.

Cleavage of HMP Moiety

Alternatively, once the conjugate has reached its desired cell-type, the HMP moiety may be cleaved from the conjugate to release the HMP moiety to the targeted cell type. For this to be achieved, the person skilled in the art will adapt the linkage-moiety to be used for cleavage to be carried out once the conjugate has reached the appropriate cell type and release the HMP immunomodulatory moiety.

Particularly, the cleavable linker can have cleavable unit that is a photocleavable, enzyme-cleavable or chemically-cleavable unit. For example, the cleavable linker can have a cleavable unit such as a disulfide (chemically cleavable), nitrobenzo (a photocleavable unit), or amine, amide or ester (enzyme-sensitive cleavable units). More particularly, the cleavable linker can be of the formula: X—S—S—Z, or, more particularly:

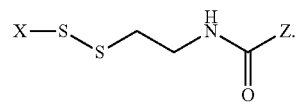

Immunogen

In accordance with a particular embodiment of the invention, the functional molecule conjugated to HMP is an immunogen, particularly an immunogen expressed by, or derived from, an infectious agent, such as for example an infectious bacterial, viral or parasitic pathogens, including Gram-negative bacterial pathogens belonging to the genus *Neisseria* (including *Neisseria meningitidis, Neisseria gonorrhoeae*), *Escherichia* (including *Escherichia coli*), *Klebsiella* (including *Klebsiella pneumoniae*), *Salmonella* (including *Salmonella typhimurium*), *Shigella* (including *Shigella dysenteriae, Shigella flexneri, Shigella sonner*), *Vibrio* (including *Vibrio cholerae*), *Helicobacter* (including *Helicobacter pylori*), *Pseudomonas* (including *Pseudomonas aeruginosa*), *Burkholderia* (including *Burkholderia multivorans*), *Haemophilus* (including *Haemophilus influenzae*), *Moraxella* (including *Moraxella catarrhalis*), *Bordetella* (including *Bordetella pertussis*), *Francisella* (including *Francisella tularensis*), *Pasteurella* (including *Pastourelle multocida*), *Legionella* (including *Legionella pneumophila*), *Borrelia* (including *Borrelia burgdorferi*), *Campylobacter* (including *Campylobacter jejuni*), *Yersinia* (including *Yersinia pestis* and *Yersinia enterocolitica*), *Rickettsie* (including *Rickettsia rickettsii*), *Treponema* (including *Treponema pallidum*), *Chlamydia* (including *Chlamydia trachomatis, Chlamydia pneumoniae*) and *Brucella* spp., and including Gram positive bacterial pathogens belonging to the genus *Staphylococcus* (including *Staphylococcus aureus*), *Streptococcus* (including *Streptococcus pneumoniae, Streptococcus pyogenes*), *Listeria* (including *Listeria monocytogenes*), *Corynebacterium* (including *Corynebacterium diphtheriae*), *Enterococcus* (including *Enterococcus faecalis*), *Clostridium* spp., and *Mycobacterium* (including *Mycobacterium tuberculosis, Mycobacterium leprae, Mycobacterium avium*).

Immunogens may also be derived from pathogenic viruses including Adenoviridae (including Adenovirus), Herpesviridae (including Epstein-Barr virus, Herpes Simplex Viruses, Cytomegalovirus, or Varicella Zoster virus), Papillomviridae, Poxviridae (including Papillomavirus), Hepadnaviridae (including Hepatitis B virus), Parvoviridae, Astroviridae, Caliciviridae, Picornaviridae (including Coxsackievirus, Hepatitis A virus, Poliovirus), Coronaviridae, Flaviviridae (including Hepatitis C virus, Dengue virus), Togaviridae (including Rubella virus), Hepeviridae, Retroviridae (including HIV), Orthomyxoviridae (including influenza virus, Arenaviridae, Bunyaviridae, Filoviridae, Paramyxoviridae (including Measles virus, Mumps virus, Parainfluenza virus, Respiratory Syncytial virus), Rhabdoviridae (including Rabies virus) or Reoviridae.

Immunogens may also be derived from pathogenic fungal infections including those caused by *Candida, Aspergillus, Cryptococcus, Histoplasma, Pneumocystis,* or *Coccidioides*. Vaccines may also target parasitic pathogens including *Leishmania, Plasmodium, Toxoplasma, Trypanosoma* and *Schistosoma*.

The immunogen may be derived from a protein or other molecules expressed on or within the subject's own cells, such as a tumor-specific immunogen or cancer-specific immunogen, to stimulate an immune response against the pathogenic cells or tissues. In one embodiment, the HBP may be introduced directly into a tumor to increase the immune response against the tumor.

According to a particular embodiment, the HMP-immunogen conjugate of the invention can be administered as part of a vaccine formulation.

Markers or Labels

In accordance with a particular embodiment, the linker of the invention is conjugated to a marker, such as, for example, a label or a tag. Particularly, the marker or tag is chosen from fluorescent and/or enzymatic tags, such as but not limited to: biotin, rhodamine, fluorescein, CF tags, EvoBlue, rhodopsin, GFP, fluorescent red, fluorescent orange biotin or other labels such as, for example:

Atto Labels
Carbohydrate Labels
CF Dyes
Fluorescein and Derivatives
Fluorescent Red and Orange Labels - (17)
Mega Labels
Metal Complexes
Other Fluorescent Labels
Phycobili Proteins
Rhodamine and Derivatives
Tracy Labels (see www.sigmaaldrich.com/life-science/biochemicals/biochemical-products.html?TablePage=16187968)

Most particularly, the compound of formula (I) is chosen from:

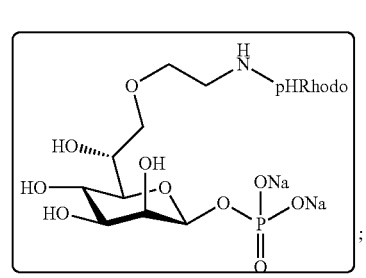

JS13a

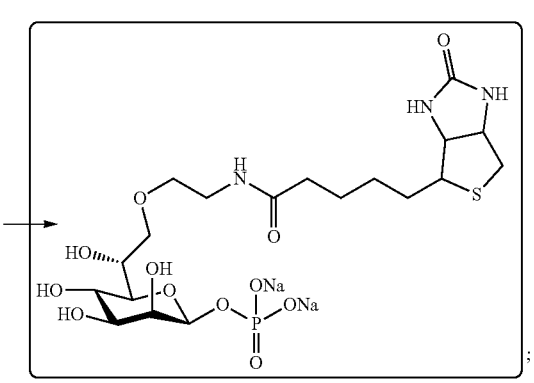

JS14a

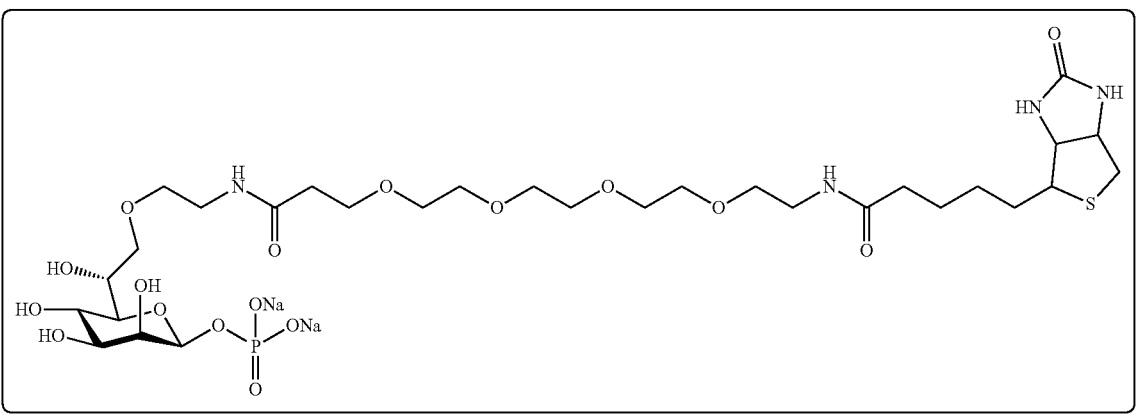
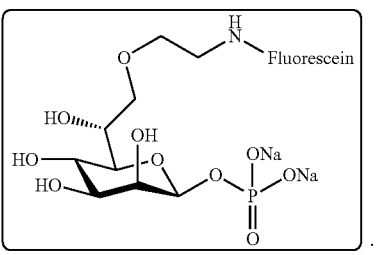
Synthesis
In accordance with an alternative aspect of the invention, there is provided a method for the synthesis of a compound of formula (I) comprising the steps of:
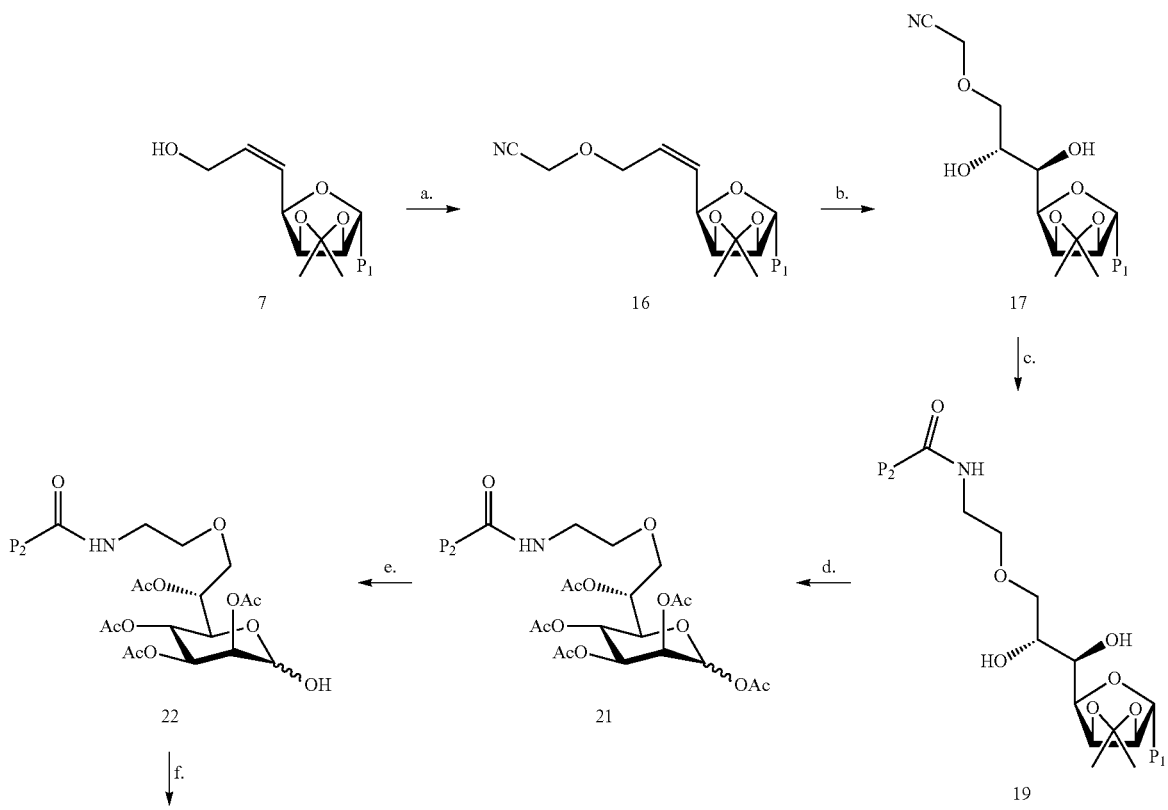

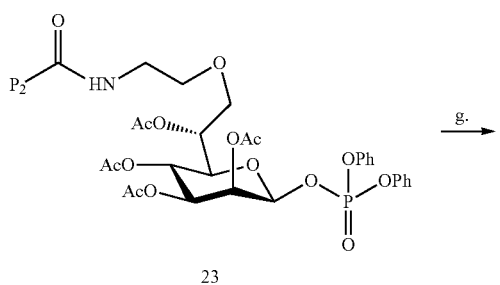

23

-continued

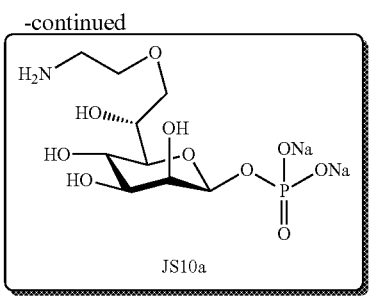

JS10a

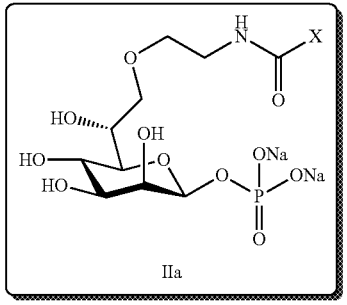

IIa

Compound 7 was synthesized as described in Sauvageau et al., Carbohydr. Res., 2017, 450, 38-43 [18]. In short:
a) the hydroxy of compound 7 was protected with a cyanoethyl moiety before
b) hydroxylation of the double bond;
c) then the nitrile was reduced to the amine and was protected with a P1 protecting group;
d) cleavage of the acetonide and P1 group followed by acetylation gave acetylated compound 21;
e) after deprotection of the anomeric acetyl; and
f) phosphorylation;
g) the compound was globally deprotected to form JS10a;
j) conjugation to molecule X activated ester gave (IIa) corresponding to a specific compound of formula (II).

A variety of linkers are synthesized to understand how the nature of the linker may impact the biological activity. With this knowledge, a vast array of functional molecules are appropriately attached to an HMP-linker to examine several aspects of this PAMP's interaction with the immune system and to augment and specifically target the linked entities processing within the immune system.

These can include but are not limited to, the identification of the receptor for HMP, an understanding of the processing of HMP, developing antibodies to HMP to follow the trafficking of the molecule, or targeting HMP to certain cells within the immune system by linking to a fluorescent moiety for example.

In accordance with a further aspect of the invention, there is provided a method for the preparation of a therapeutic conjugate having modulated immunomodulatory activity, the method comprising the step of: conjugating a functional molecule with a compound of formula (I) or (Ia) as defined herein.

The conjugates of the present invention can be synthesized via the synthesis of HMP that is significantly simpler and likely more commercially realisable than that of HBP.

Compound for Use and Uses

In accordance with a further aspect of the invention, there is provided a conjugate compound of formula (II) or (IIa) as defined herein, for use in targeting and/or modulating an immune response in a subject. Particularly, the ability to target the modulation of the immune response of the subject is useful for preventing, treating, ameliorating, or inhibiting an injury, disease, disorder or condition wherein the modulation of the immune response is beneficial.

According to a particular embodiment, the conjugate compound for use is carried out in the context of a vaccine for the treatment or prevention of disease.

In accordance with a further aspect of the invention, there is provided a use of an effective amount of a conjugate, also called a compound of formula (II) or (IIa) as defined herein, for targeting and/or modulating an immune response in a subject. Particularly, the modulation of the immune response of the subject is useful for preventing, treating, ameliorating, or inhibiting an injury, disease, disorder or condition wherein the modulation of the immune response is beneficial.

According to a particular embodiment, the use of the compound is carried out in the context of a vaccine for the treatment or prevention of disease.

Alternatively, the use of the compound of formula (II) or (IIa as defined herein, is carried out for the manufacture of a medicament for modulating an immune response in a subject.

Particularly, in the context of the use of the conjugate of the invention, the immune response of the subject is enhanced. In this embodiment, the molecule conjugated to the HMP-linker is an antigen or an immunogen, more particularly chosen from cell-differentiation antigen, or antigens from cancer cells, bacteria, viruses or parasites.

More particularly, the immunogen used for embodying the invention is from Gram-negative bacteria, most particularly chosen from: *Neisseria, Escherichia, Klebsiella, Salmonella, Shigella, Vibrio, Helicobacter, Pseudomonas, Burkholderia, Haemophilus, Moraxella, Bordetella, Francisella, Pasteurella, Borrelia, Campylobacter, Yersinia, Rickettsia, Treponema, Chlamydia* and *Brucella.*

Still more particularly, the immunogen useful for the invention is from Gram-positive bacteria, most particularly chosen from: *Staphylococcus, Streptococcus, Listeria, Corynebacterium, Enterococcus, Clostridium* and *Mycobacterium.*

Alternatively, the immunogen used for embodying the present invention is derived, or comes, from a virus, more particularly chosen from: Adenoviridae, Herpesviridae, Papillomviridae, Poxviridae, Hepadnaviridae, Parvoviridae, Astroviridae, Caliciviridae, Picornaviridae, Coronaviridae, Flaviviridae, Togaviridae, Hepeviridae, Retroviridae, Orthomyxoviridae, Arenaviridae, Bunyaviridae, Filoviridae, Paramyxoviridae, Rhabdoviridae, Reoviridae and Human Immunodeficiency (HIV) viruses.

Still, according to an alternative embodiment, the immunogen is from a parasite, more particularly chosen from: *Leishmania, Plasmodium, Toxoplasma, Trypanosoma* and *Schistosoma*.

Still, alternatively, the immunogen may originate from a cancer-specific antigen, more particularly some or all of the cancer-specific antigens listed in Table 1:

According to an alternative embodiment, there is provided a use of the conjugate compound of the invention, wherein the immune response of the subject is decreased, more particularly in the case where the immune response is provoked by an inflammatory response or an allergic reaction to a foreign element. In this case, the compound of the invention is conjugated with an immune-inhibitory molecule.

Method of Treatment or Prevention

In accordance with a further aspect, there is provided a method for modulating an immune response in a subject, comprising administering an effective amount of the compound of formula (II) or (IIa) as defined herein to a subject suffering therefrom.

In accordance with a particular aspect, the modulation of immune response is necessary (or indicated or prescribed by

TABLE 1

(cancer-specific antigen useful for conjugating with HMP-linker

| Category | Example Antigen | Cancer Histology |
| --- | --- | --- |
| Oncofetal | CEA | Colorectal carcinoma |
| | Immature laminin receptor | RCC |
| | TAG-72 | Prostate carcinoma |
| Oncoviral | HPV E6, E7 | Cervical carcinoma |
| Overexpressed/accumulated | BING-4 | Melanoma |
| | Calcium-activated chloride channel 2 | Lung carcinoma |
| | Cyclin-$B_1$ | Multi |
| | 9D7 | RCC |
| | Ep-CAM | Breast carcinoma |
| | EphA3 | Multi |
| | Her2/neu | Multi |
| | Telomerase | Multi |
| | Mesothelin | Ductal pancreatic carcinoma |
| | SAP-1 | Colorectal carcinoma |
| | Survivin | Multi |
| Cancer-Testis | BAGE family | Multi |
| | CAGE family | Multi |
| | GAGE family | Multi |
| | MAGE family | Multi |
| | SAGE family | Multi |
| | XAGE family | Multi |
| CT9, CT10 | | Multi |
| | NY-ESO-1/LAGE-1 | Multi |
| | PRAME | Multi |
| | SSX-2 | Melanoma, Multi |
| Lineage Restricted | Melan-A/MART-1 | Melanoma |
| | Gp100/pmel17 | Melanoma |
| | Tyrosinase | Melanoma |
| | TRP-1/-2 | Melanoma |
| | P.polypeptide | Melanoma |
| | MC1R | Melanoma |
| | Prostate-pecific antigen | Prostate |
| Mutated | β-catenin | Melanoma, Prostate, HCC |
| | BRCA1/2 | Breast, ovarian carcinoma |
| | CDK4 | Multi |
| | CML66 | CML |
| | Fibronectin | Multi |
| | MART-2 | Melanoma |
| | p53 | Multi |
| | Ras | Multi |
| | TGF-βRII | Colorectal carcinoma |
| Posttranslationally altered | MUC1 | Ductal carcinoma, RCC |
| Idiotypic | Ig, TCR | B, T leukemia, lymphoma, myeloma |

BRCA = breast cancer antigen; CDK4 = cyclin-dependent kinase-4; CEA = carcino-embryonic antigen; CML66 = chronic myelogenous leukemia (antigen) 66; CT = cancer testis; HPV = human papilloma virus; Ep-CAM = epithelial cell adhesion molecule; Ig = immunoglobulin; MART-1/-2 = melanoma antigen recognized by T cells-1/-2; MC1R = melanocortin-1-receptor; SAP-1 = stomach cancer-associated protein tyrosine phosphatase-1; TAG-72 = tumor antigen-72; TCR = T cell receptor; TGF-βRII = transforming growth factor-β receptor II; TRP = tyrosinase-related protein.

a treating physician) for increasing an immune response to an infection caused by: bacteria, virus, or parasites, such as those defined herein above.

Alternatively, the modulation of immune response is necessary (or indicated or prescribed by a treating physician) for decreasing an immune response such as inflammation or an allergic reaction in a subject.

Particularly, the subject is a human.

In accordance with a particular embodiment, there is provided a method for the treatment of HIV comprising the steps of: administering an HMP-conjugated to an anti-HIV molecule, wherein the HMP moiety stimulates HIV latently-infected cells to start producing virus, and wherein the anti-HIV molecule kills the produced virus; whereby the HMP-anti-HIV conjugate eradicates the latent viral pool and treats the HIV infection.

In accordance with an alternative embodiment, there is provided a method for the treatment of HIV comprising the steps of: administering an HMP-conjugated to an HIV-reservoir cell-specific antigen binding partner to a subject, and treating said subject with an anti-HIV drug, wherein the conjugate-HMP moiety stimulates HIV latently-infected cells to start producing virus, and the anti-HIV drug kills the produced virus; whereby the HMP-anti-HIV conjugate eradicates the latent viral pool and treats the HIV infection.

Particularly, the anti-HIV molecule or drug is chosen from: Nucleoside/Nucleotide reverse transcriptase inhibitors (NNRTI), Multiclass inhibitors, Non-nucleoside reverse transcriptase inhibitors (NNRTIs), Protease inhibitors (PI), Entry inhibitors, Chemokine co-receptor antagonists (CCR5 antagonists), Cytochrome P4503A (CYP3A) inhibitors. More particularly, the anti-HIV drug is as defined herein above.

The present invention is illustrated in further details by the following non-limiting examples.

EXAMPLES

The following examples are put forth to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Chemical Synthesis

Figure 1B:
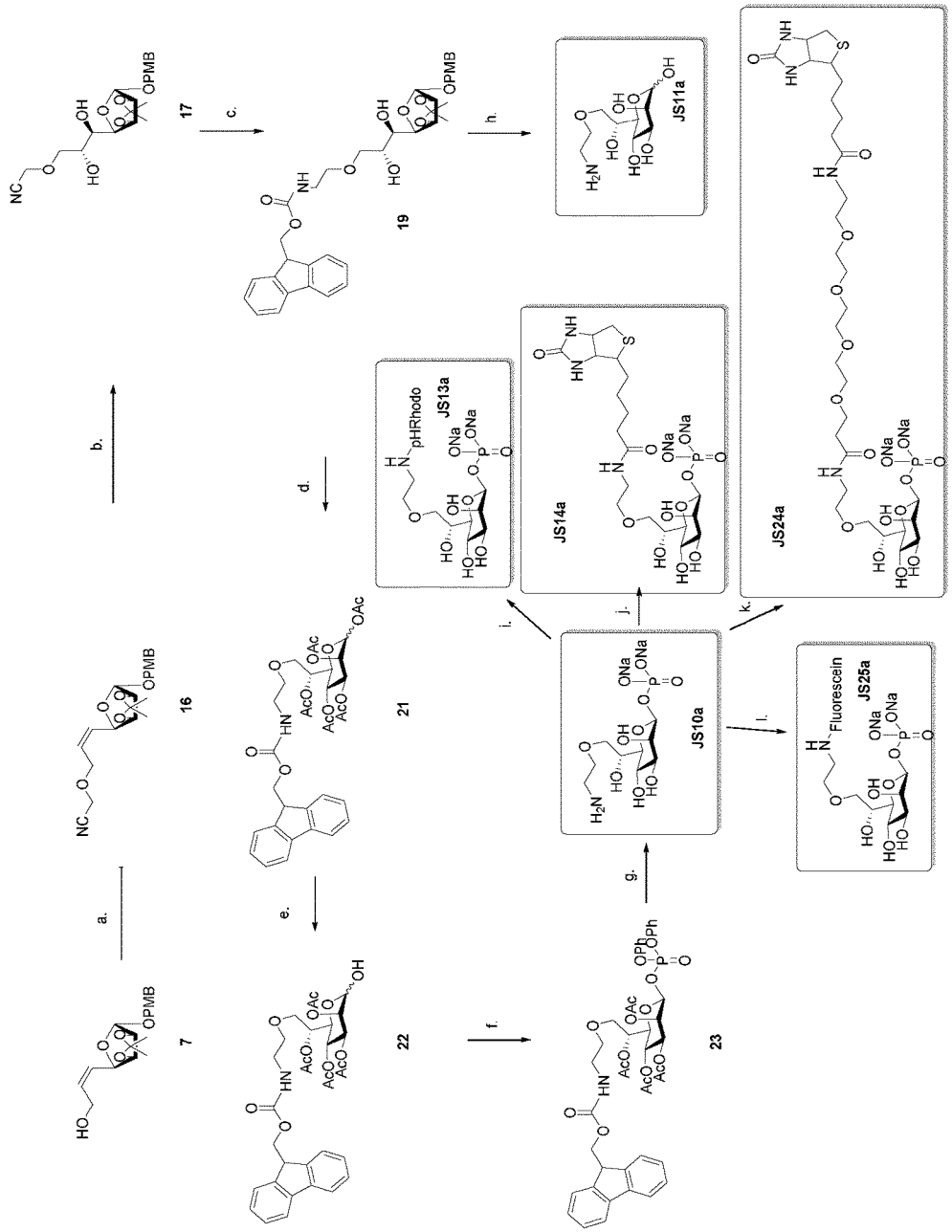
FIG. 1B. Reaction scheme 2 for the synthesis of particular embodiments of derivative linkers of HMP-β.
Figure 2:
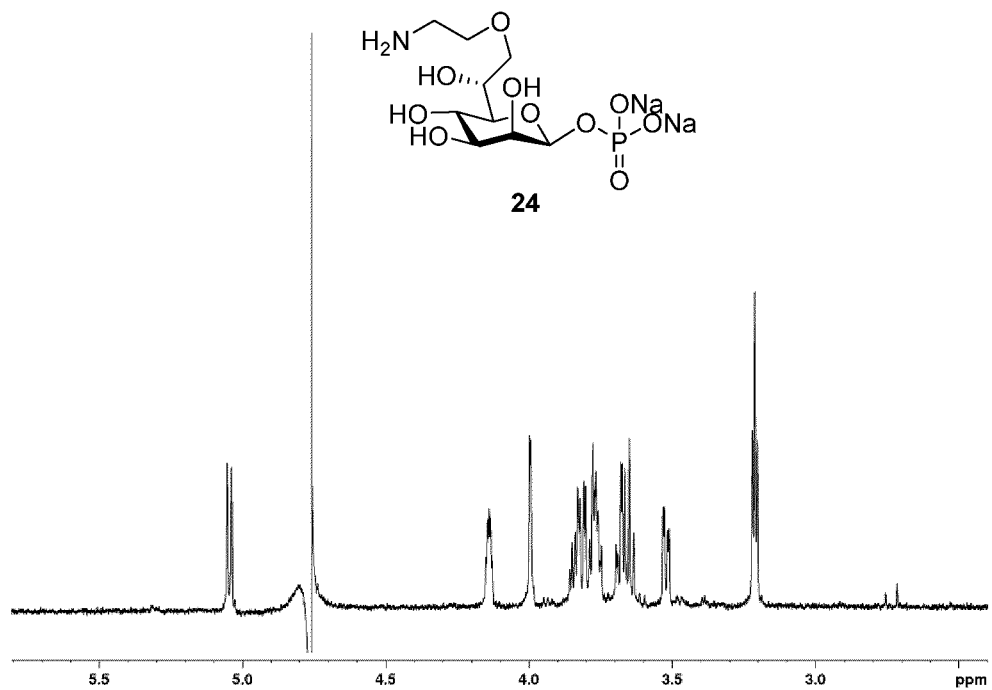
FIGS. 2A-B: A) $^1$H NMR spectra of 7-O-(Aminoethyl)-D-Glycero-β-D-manno-heptopyranosyl phosphate (JS10); B) HSQC $^1$H-$^{13}$C, NMR spectra of compound JS10.
Figure 2:
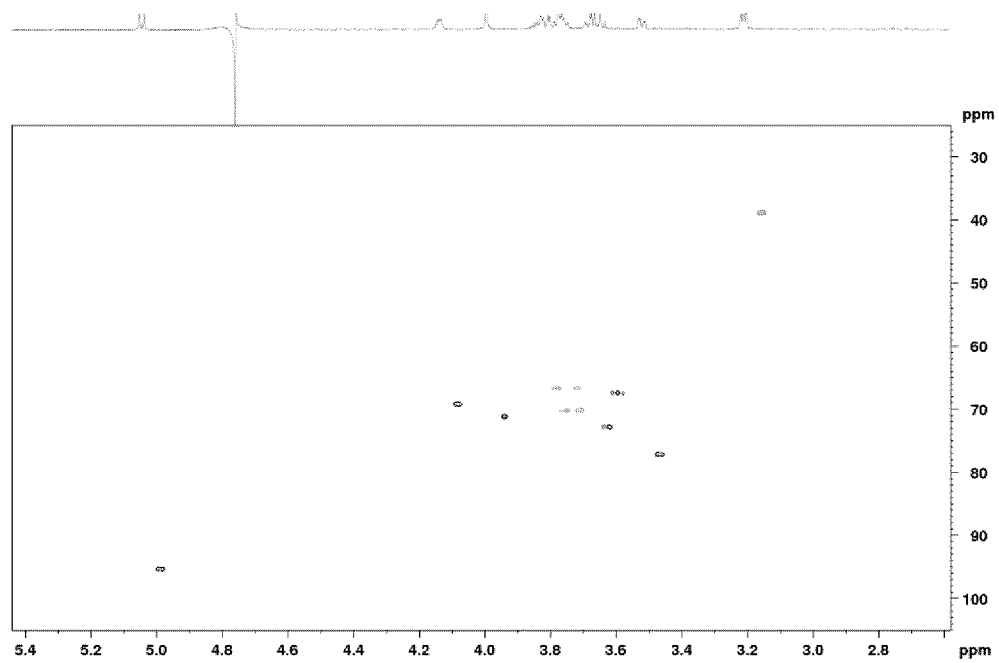
Figure 3A:
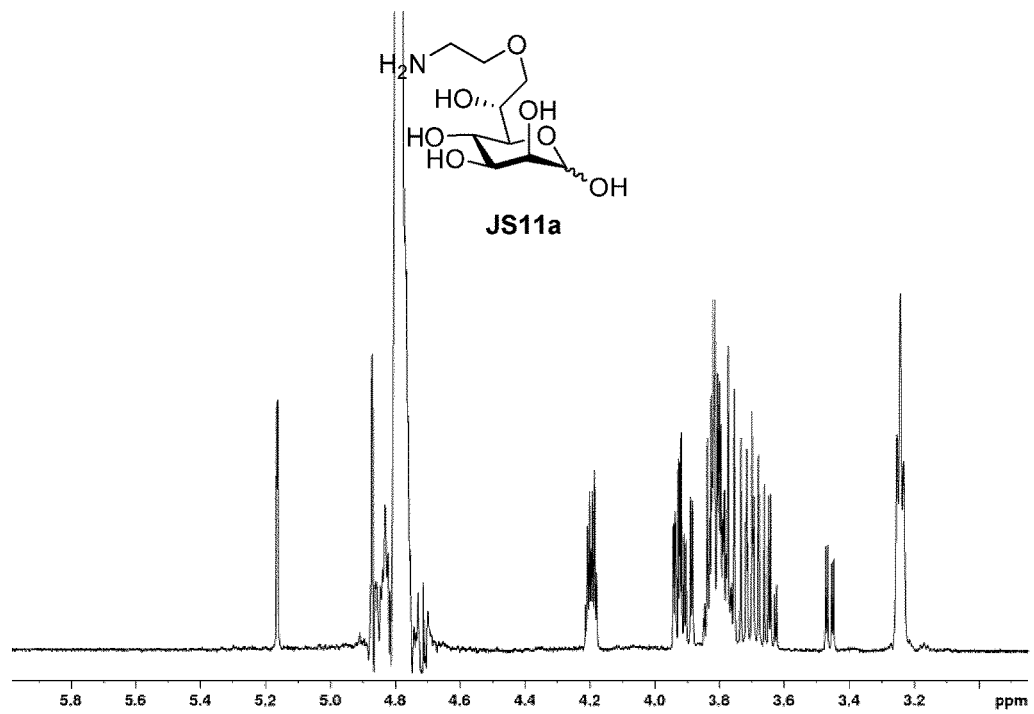
FIGS. 3A-B. A) $^1$H NMR spectra of 7-O-(Aminoethyl)-D-Glycero-D-manno-heptopyranose (JS11a). B) $^{13}$C NMR spectra of 7-O-(Aminoethyl)-D-Glycero-D-manno-heptopyranose (JS11a).
Figure 3B:
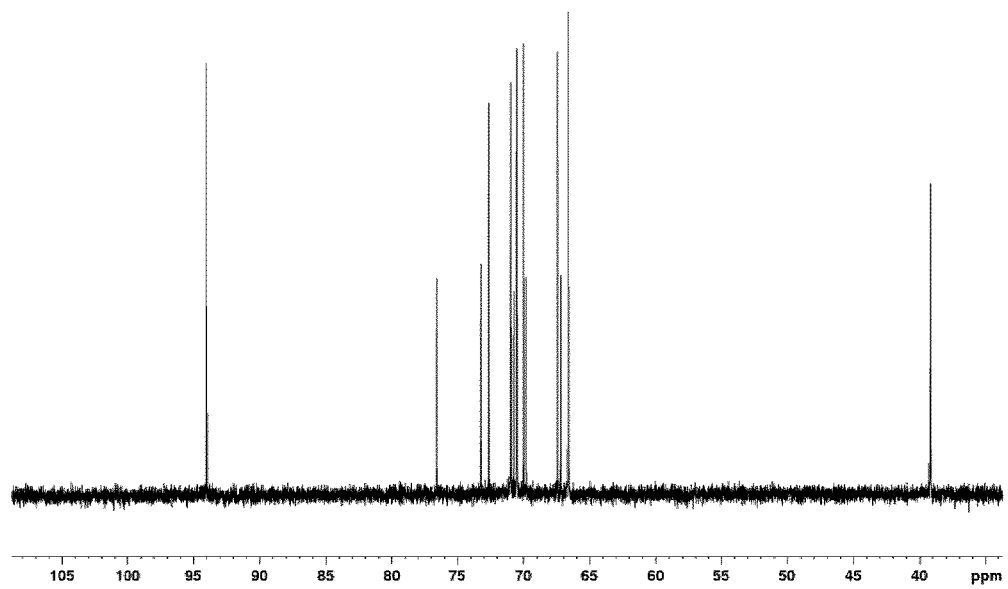
Figure 4A:
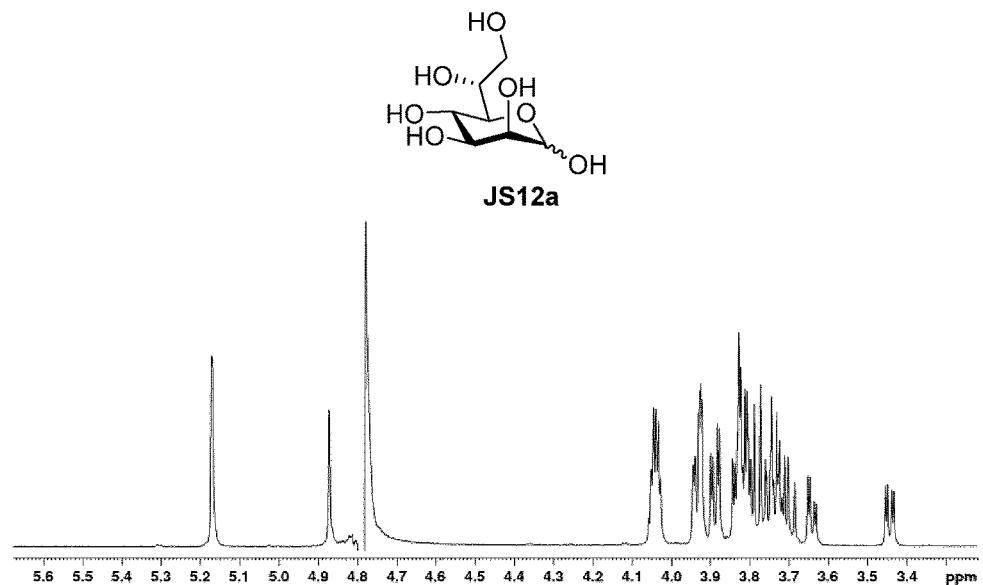
FIGS. 4A-B. A) $^1$H NMR spectra of D-glycero-D-manno heptose (JS12a). B) $^{13}$C NMR spectra of D-glycero-D-manno heptose (JS12a).
Figure 4B:
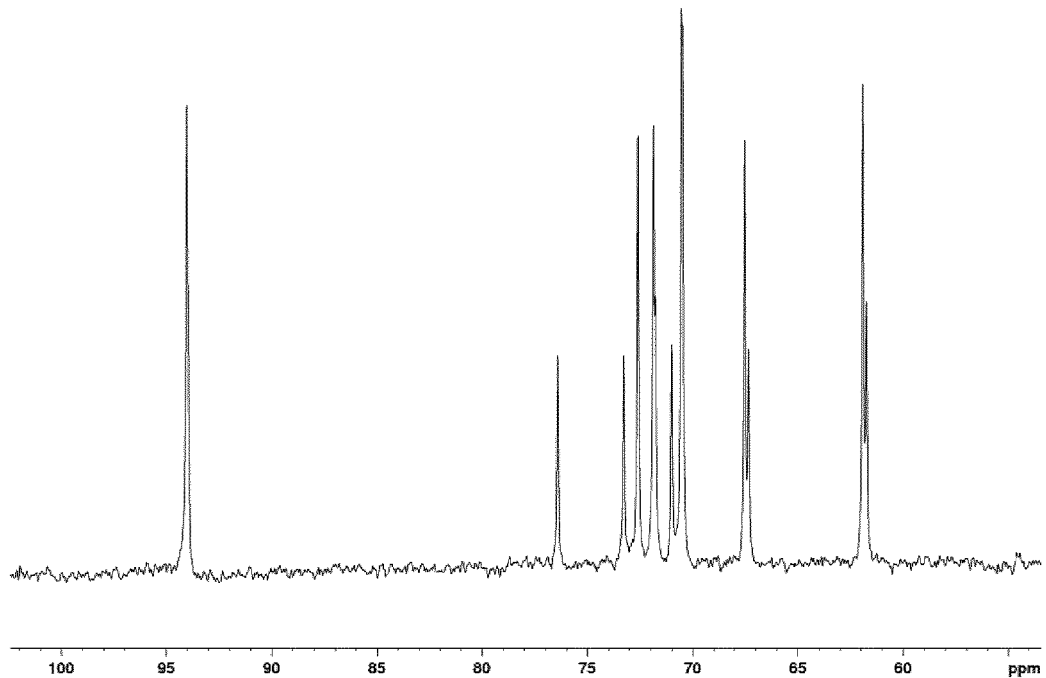
Figure 5A:
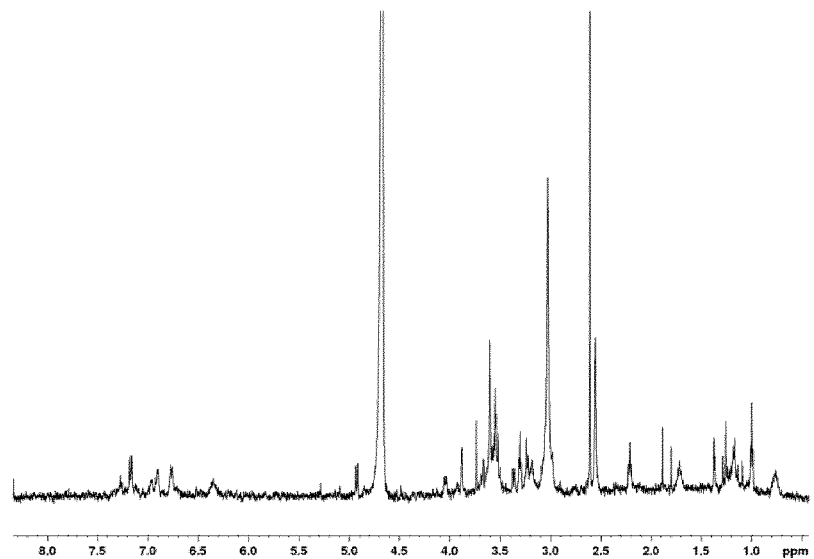
FIGS. 5A-C. A) $^1$H NMR spectra of 7-O-(Aminoethyl-pH-Rhodo)-D-Glycero-β-D-manno-heptopyranosyl phosphate (JS13a). B) LMRS spectra of 7-O-(Aminoethyl-pH-Rhodo)-D-Glycero-β-D-manno-heptopyranosyl phosphate (JS13a). C) HPLC chromatogram of 7-O-(Aminoethyl-pH-Rhodo)-D-Glycero-β-D-manno-heptopyranosyl phosphate (JS13a).
Figure 5B:
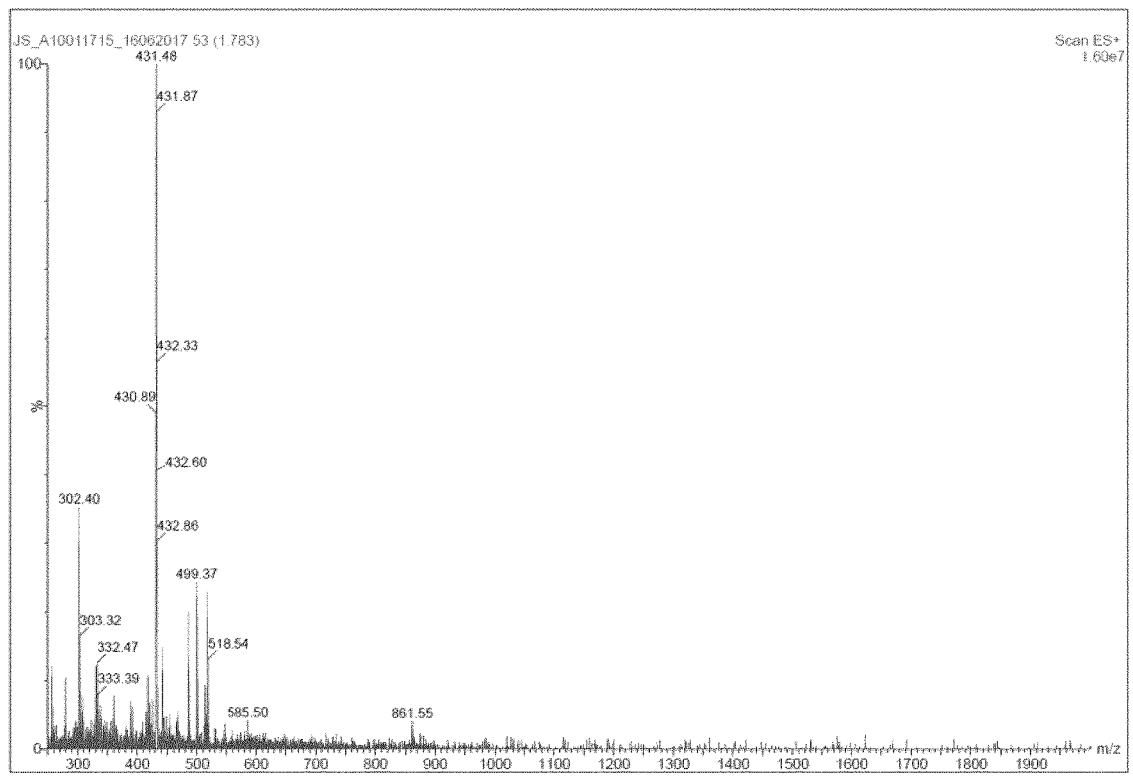
Figure 5C:
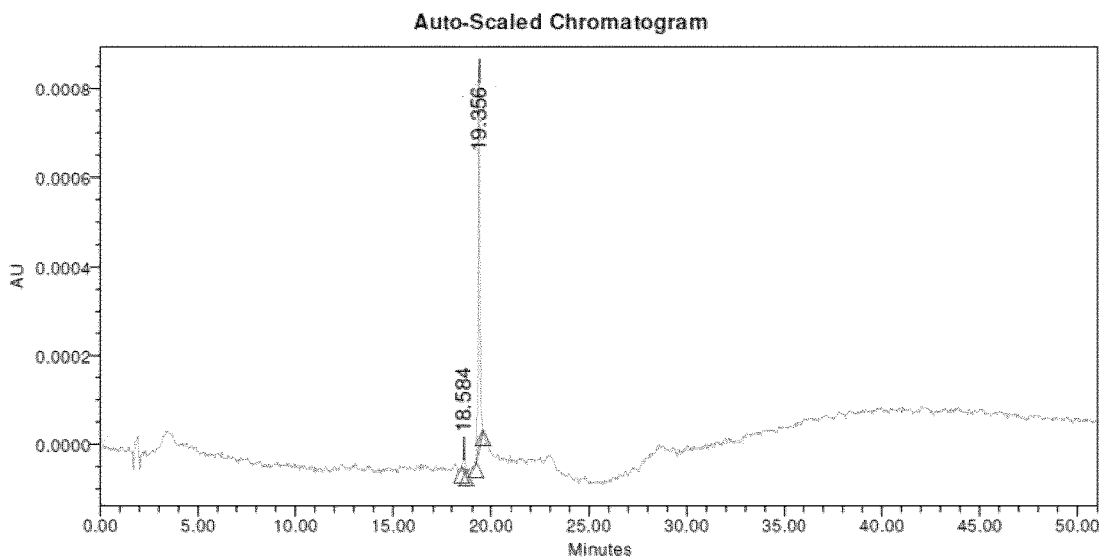
Figure 6A:
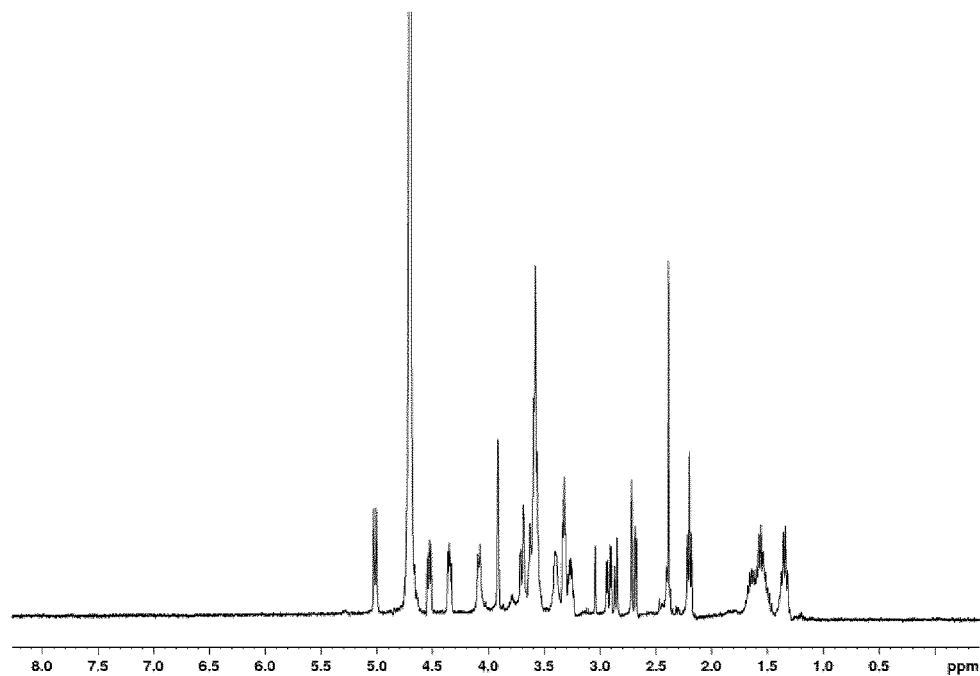
FIGS. 6A-B. A) $^1$H NMR spectra of 7-O-([Biotin]amidoethyl)-D-Glycero-β-D-manno-heptopyranosyl phosphate (JS14a). B) $^{13}$C NMR spectra of 7-O-([Biotin]amidoethyl)-D-Glycero-β-D-manno-heptopyranosylphosphate (JS14a).
Figure 6B:
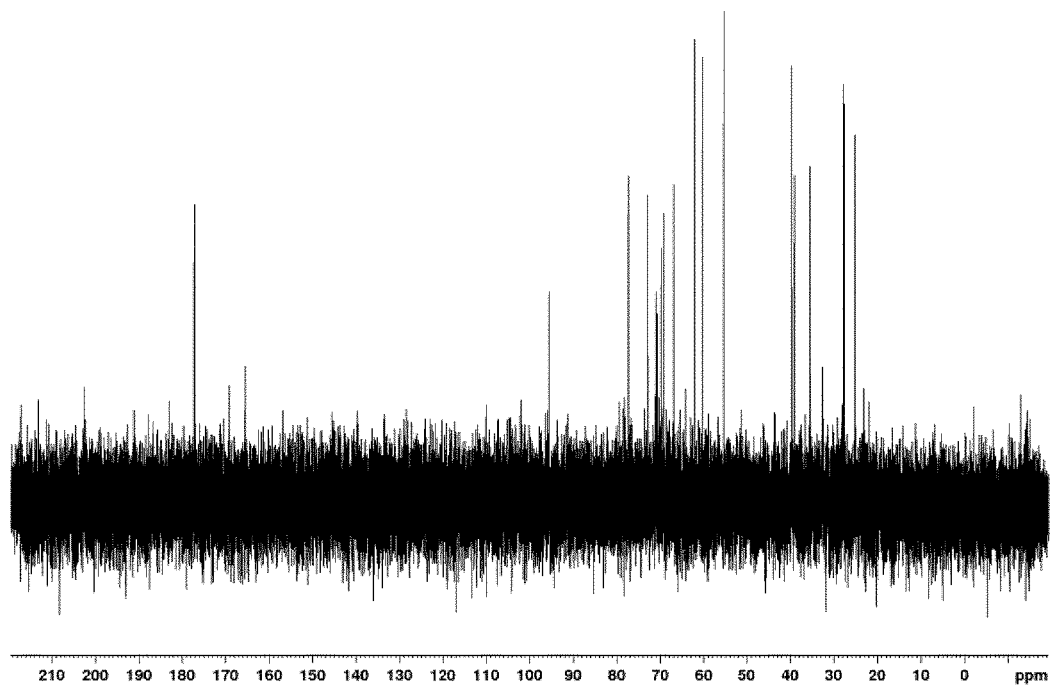
Figure 7:
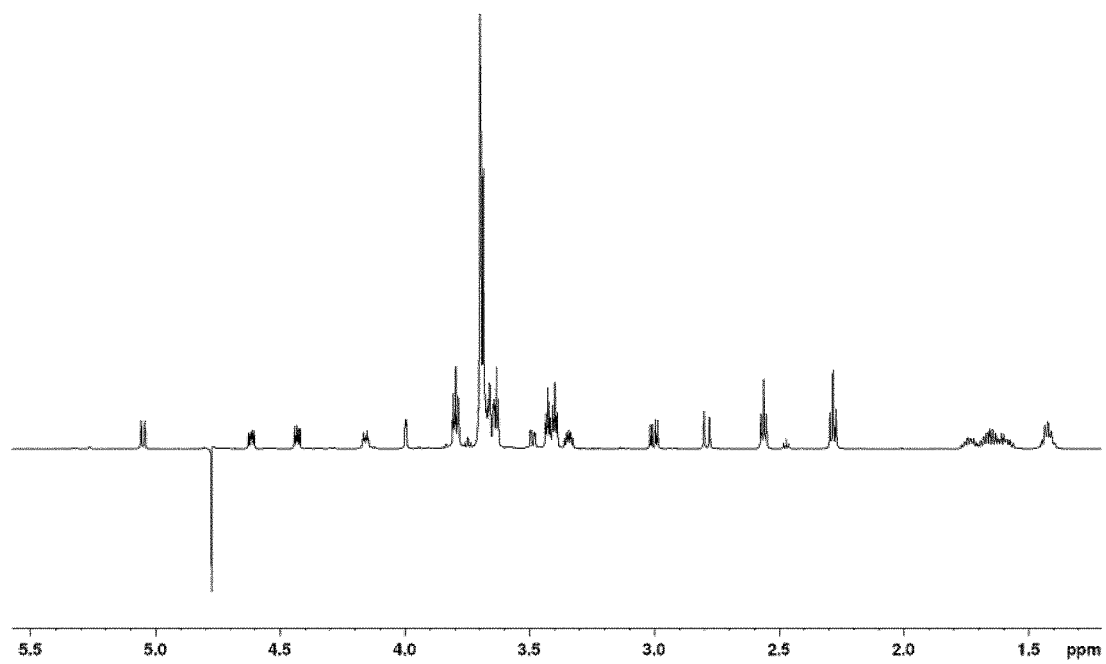
FIG. 7. $^1$H NMR spectra of 7-O-([Biotin]-dPEG4-amidoethyl)-D-Glycero-β-D-manno-heptopyranosyl phosphate (JS24a)
Figure 8:
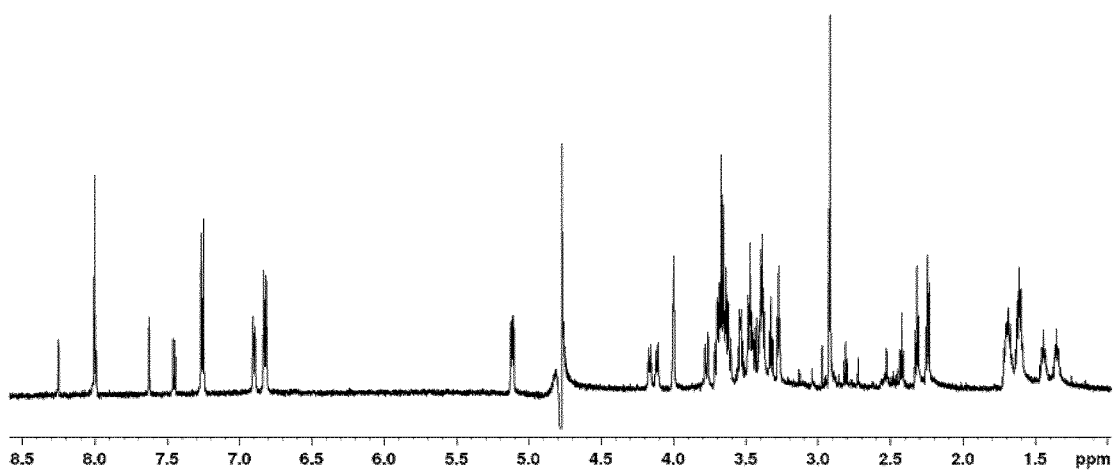
FIG. 8. $^1$H NMR spectra of 7-O-([Fluorescein]-amidoethyl)-D-Glycero-β-D-manno-heptopyranosyl phosphate (JS25a)

The molecules where data were obtained from are depicted in boxes in Scheme 2 (also shown as FIG. 1B) (JS10a, JS11a, JS13a, JS14a, JS24a, JS25a). JS12a refers to D-glycero-D-manno heptose control.

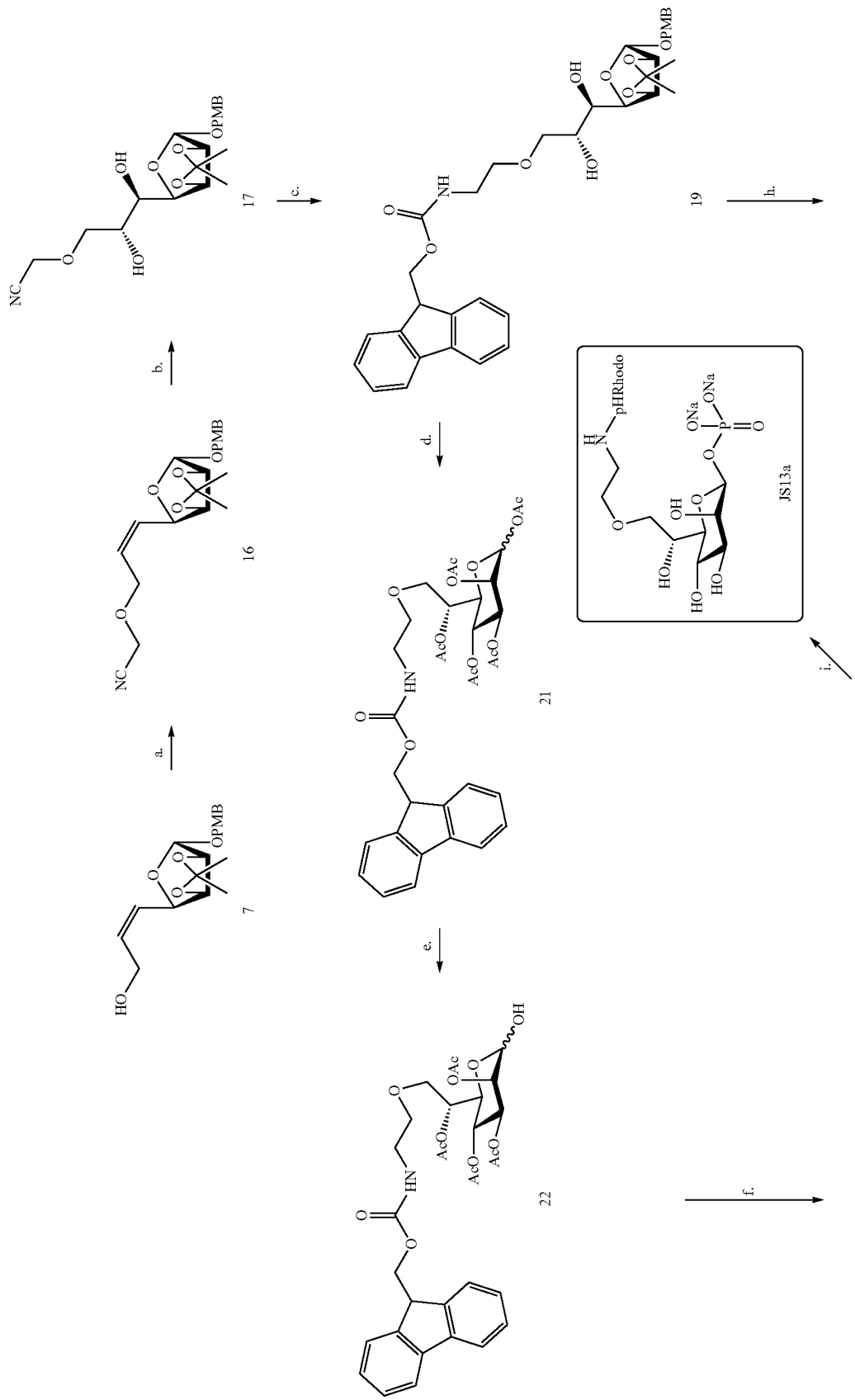

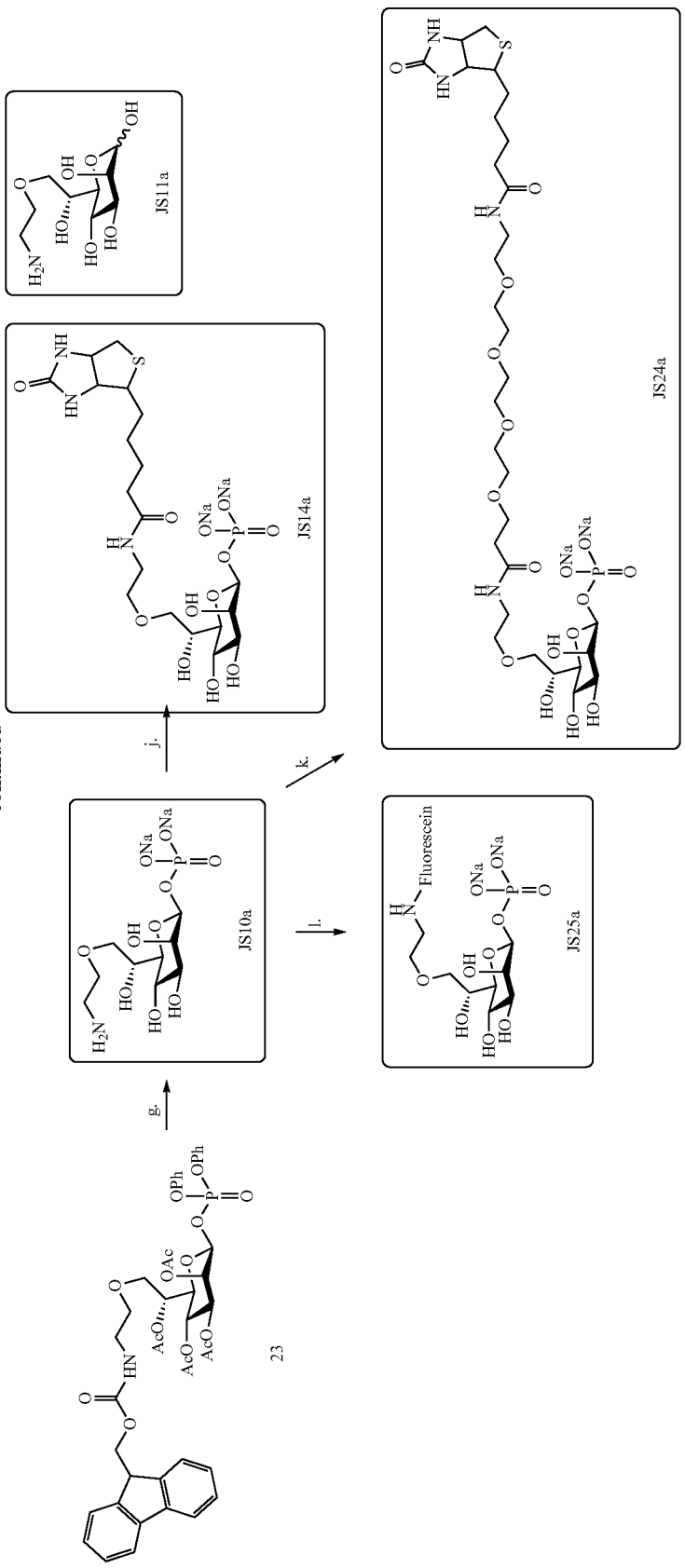

a. NaH, BrCH$_2$CN, ACN, 0° C,
b. OsO$_4$, NMMO, Dioxane:Acetone:Water,
c. BH$_3$—Me$_2$S, THF, FMOCCl,
d. DCM:TFA:Water, then 10% piperidine,
e. HBr•AcOH, AcOH, DCM,
f. DIPEA, Ammonium acetate in DMF,
g. PtO$_2$/C, H$_2$, then TEA, MeOH.
h. DCM:TFA:Water, then DMF, Piperidine.
i. 1xPBS:DMSO (1:1), pHRhodo activated ester
j. Water:DMF (5:3), Et$_3$N, (+)-Biotin N-hydroxysuccinimide ester,
k. Biotin-dPEG4-TFP ester, Water:DMF (5:1), NaHCO$_3$
l. Fluorescein activated ester, Water:DMF (5:1), NaHCO$_3$

[Methoxybenzyl-7-O-cyanoethyl-(Z)-5,6-dioxy-2,3-O-isopropylidene-α-D-lyxo-hept-5-enofuranosid] uronate (16)

Previously co-evaporated compound 7 (523 mg, 1.6 mmol) was dissolved in acetonitrile (7 mL) and cooled down to 0° C. Sodium hydride (270 mg, 60% dispersion in mineral oil, 6.7 mmol) was added in portions and the mixture was stirred for 30 minutes. Bromoacetonitrile (500 μL, 2.4 mmol) was added dropwise to the solution still kept at 0° C. The reaction mixture turned slowly dark brown and was shown to be completed after 5 hours (Rf=0.5, ethyl acetate:hexane, 2:3, v:v). Methanol (5 ml) was added slowly on ice and the reaction mixture was warmed up. The reaction mixture was dissolved in DCM, washed with water and brine and the organic layer was dried using magnesium sulfate. After concentration in vacuo, the compound was purifier using flash chromatography to give compound 16 in 88% yield (525 mg, 1.4 mmol). $[α]^{25}$=46.7 (c=0.01, $CH_3Cl_3$), $^1H$ NMR (600 MHz, $CDCl_3$): δ=7.25 ($J_{CHCCH2, CHCOMe}$=8.6 Hz, d, 2H, $CHCCH_2$, PMB), 6.86 ($J_{CHCOMe, CHCCH2}$=8.7 Hz, d, 2H, $CHCOMe$, PMB), 5.99 (m, 1H, H5'), 5.82 (m, 1H, H6'), 5.09 (s, 1H, H1'), 4.73 ($J_{H4',H3'}$=3.6 Hz, $J_{H4',H5'}$=8.0 Hz, dd, 1H, H4'), 4.73 ($J_{H3',H2'}$=5.7 Hz, $J_{H3',H4'}$=3.9 Hz, dd, 1H, H3'), 4.63 ($J_{H2', H3'}$=5.6 Hz, d, 1H, H2'), 4.62 ($J_{CHA, CHB}$=10.7 Hz, ABX, 1H, CHA, PMB), 4.44 ($J_{CHB, CHA}$=11.5 Hz, ABX, 1H, CHB, PMB), 4.24 ($J_{H7A',H6'}$=1.4 Hz, ABX, 1H, H7A'), 4.23 ($J_{H7B',H6'}$=1.4 Hz, $J_{H7B',H6'}$=6.5 Hz, ABX, 1H, H7B'), 4.22 (s, 2H, $CH_2CN$), 3.77 (3H, m, $CH_3O$, PMB), 1.44 (3H, s, $CH_3COCH_2',OCH_3$), 1.28 (3H, s, $CH_3COCH_2',OCH_3$). $^{13}C$ NMR (150 MHz, $CDCl_3$) δ=159.6 ($COMe$, PMB), 130.0 ($CHCCH_2$ PMB), 129.7 ($C$, PMB and C5'), 128.4 (C6'), 116.2 ($CN$), 114.2 ($CHCCH_2$ PMB), 112.8 (C2',3'MeO$_2C$), 105.4 (C1'), 85.6 (C2'), 81.6 (C3'), 75.9 (C4'), 69.1 ($CH_2$PMB), 67.2 (C7'), 55.6 (OMe, PMB), 55.2 ($CH_2CN$), 26.3 and 25.0 ($CH_3COCH_2',OCH_3'$). HRMS m/z Calcd for $C_{20}H_{25}NO_6Na$ [M+Na]$^+$ 398.1580, found 398.1586.

Methoxybenzyl-7-O-(cyanoethyl)-2,3-O-isopropylidene-D-glycero-α-D-manno heptofuranoside (17)

Alkene 16 (523 mg, 1.4 mmol) was stirred with NMMO (656 μL, 2.8 mmol, 50% in water) for 30 minutes at RT in acetone:dioxane:water (12 mL, 1:2:1, v:v:v). Then osmium tetraoxide (708 μL, 0.1 mmol, 4% in water) was added to the solution. The solution turned slowly yellow. After 5 hours, TLC monitoring showed that the reaction was completed (Rf=0.47 in ethyl acetate). The solution was diluted with DCM and was treated with ice cold HCL (5M) and then with 45% $Na_2S_2O_5$ and water. After drying the organic layer with $MgSO_4$, filtering and concentrating in vacuo, compound 16 was purified using flash chromatography. This afforded pure 17 in 57% yield (329 mg, 0.8 mmol). Rf=0.39 (Hexane:Ethyl acetate, 4:1, v:v). $[α]_D^{25}$=63.1 (c=0.01, $CH_3Cl_3$), $^1H$ NMR (600 MHz, $CDCl_3$): δ=7.25 ($J_{CHCCH2, CHCOMe}$=8.4 Hz, d, 2H, $CHCCH_2$, PMB), 6.87 ($J_{CHCOMe, CHCCH2}$=8.7 Hz, d, 2H, $CHCOMe$, PMB), 5.12 (s, 1H, H1'), 4.88 ($J_{H3',H2'}$=5.9 Hz, $J_{H3',H4'}$=3.9 Hz, dd, 1H, H3'), 4.63 ($J_{H2', H3'}$=5.7 Hz, d, 1H, H2'), 4.59 ($J_{CHA, CHB}$=11.6 Hz, ABX, 1H, CHA, PMB), 4.43 ($J_{CHB, CHA}$=11.6 Hz, ABX, 1H, CHB, PMB), 4.34 (s, $CH_2CN$), 4.13 ($J_{H4',H3'}$=3.6 Hz, $J_{H4',H5'}$=7.1 Hz, dd, 1H, H4'), 4.05-3.98 (H5', H6'), ($J_{H7',H6'}$=2.4 Hz, $J_{H7A',H7B'}$=9.8 Hz, dd, 1H, H7A'), 3.82-3.77 (4H, m, $CH_3O$ and H7B'), 1.47 (3H, s, $CH_3COCH2',OCH3$), 1.31 (3H, s, $CH_3COCH2',OCH3$). $^{13}C$ NMR (150 MHz, $CDCl_3$) δ=159.8 ($COMe$, PMB), 130.0 ($CHCCH_2$ PMB), 129.5 ($C$ PMB), 116.1 ($CN$), 114.3 ($CHCCH_2$ PMB), 113.1 (C2',3'MeO$_2C$), 105.7 (C1'), 85.0 (C2'), 80.8 (C3'), 79.4 (C4'), 72.9 (C7'), 72.6 (C6'), 70.5 (C5'), 69.3 ($CH_2$PMB), 57.2 ($CH_2CN$), 55.6 (OMe, PMB), 26.3 and 24.9 ($CH_3COCH_2',OCH_3'$). HRMS m/z Calcd for $C_{20}H_{27}NO_8Na$ [M+Na]$^+$ 432.1634, found 432.16451.

Methoxybenzyl-7-O-(FMOC-aminoethyl)-2,3-O-isopropylidene-D-glycero-α-D-manno heptofuranoside (19)

Nitrile 17 (196 mg, 479 μmol) was coevaporated with toluene and then dissolved in THF (5 mL). To the mixture was added slowly borane-dimethyl sulfide (182 μL, 1.9 mmol). After 3 hours at 80° C., the solution was cooled at 0° C. and methanol was slowly added (5 mL). After 16 hours, the solution was concentrated in vacuo and the compound was dissolved in dioxane (1.3 mL) and a $NaHCO_3$ (sat. aq.) solution (2.6 mL). FMOCCl (258 mg, 1 mmol) was then added and the reaction was stirred for another 16 hours after which the solution was diluted using water and dichloromethane and the organic layer was washed with water and brine. After drying with $MgSO_4$ and concentrating the organic layer in vacuo, the compound was purifier using flash chromatography and afforded pure 19 in 61% yield over two steps (187 mg, 294 μmol). Rf=0.45 (Ethyl Acetate:Hexane, 4:1, v:v). $^1H$ NMR (600 MHz, $CDCl_3$): δ=7.76 ($J_{Ha, Hc}$=7.2 Hz, d, 2H, Ha, FMOC), 7.60 ($J_{Hb, Hd}$=7.7 Hz, d, 2H, Hb, FMOC), 7.39 ($J_{Hc, Ha}$=$J_{Hc, Hd}$=7.4 Hz, dd (apt), 2H, Hc, FMOC), 7.31 ($J_{Hd, Hc}$=$J_{Hd, Hb}$=7.4 Hz, dd (apt), 2H, Hd, FMOC), 7.23 ($J_{CHCCH2, CHCOMe}$=8.7 Hz, d, 2H, $CHCCH_2$, PMB), 6.86 ($J_{CHCOMe, CHCCH2}$=8.7 Hz, d, 2H, $CHCOMe$, PMB), 5.25 (N$H$), 5.12 (s, 1H, H1'), 4.89 ($J_{H3',H2'}$=5.8 Hz, $J_{H3',H4'}$=3.6 Hz, dd, 1H, H3'), 4.62 ($J_{H2', H3'}$=5.9 Hz, d, 1H, H2'), 4.58 ($J_{CHA, CHB}$=11.4 Hz, ABX, 1H, CHA, PMB), 4.42 ($J_{CHB, CHA}$=11.6 Hz, ABX, 1H, CHB, PMB), 4.39 (m, 2H, ABX, Hf), 4.22 (m, 1H, He), 4.14 ($J_{H4',H3'}$=3.6 Hz, $J_{H4',H5'}$=7.3 Hz, dd, 1H, H4'), 4.05 ($J_{H4',H5'}$=$J_{H5',H6'}$=6.6 Hz, 1H, H5'), 3.95 (m, 1H, H6'), 3.79 (3H, s, $CH_3O$, PMB), 3.61 (m, 2H, H7'), 3.72 (m, 2H, $CH_2CH_2NH$), 3.42 (m, 2H, $CH_2NH$), 1.46 (3H, s, $CH_3COCH2',OCH3$), 1.30 (3H, s, $CH_3COCH2',OCH3$). $^{13}C$ NMR (150 MHz, $CDCl_3$) δ=159.8 ($COMe$, PMB), 144.3 ($CH_2CHC$), 141.6 ($CH_2CHCC$), 130.0 ($CHCCH_2$ PMB), 129.5 ($C$ PMB), 128.0 ($CHc$), 127.4 ($CHd$), 125.4 ($CHb$), 120.3 ($CHa$), 114.3 ($CHCCH_2$ PMB), 113.0 (C2',3'MeO$_2C$), 105.6 (C1'), 85.1 (C2'), 80.8 (C3'), 79.4 (C4'), 72.5 ($CH_2NH$), 73.3 (C6'), 71.0 (C5'), 70.9 (C7'), 69.2 ($CH_2$PMB), 67.1 (Cf), 55.6 (OMe, PMB), 47.6 (Ce), 41.1 ($CH_2NH$), 26.3 and 24.8 ($CH_3COCH2',OCH3'$). HRMS m/z Calcd for $C_{34}H_{39}NO_{14}Na$ [M+Na]$^+$ 658.2628, found 658.2696.

1,2,3,4,6-Penta-O-acetyl-[7-O-(FMOC-aminoethyl)-D-glycero-3-D-manno-heptopyranosyl (21)

Compound 19 (60 mg, 94 μmol) was stirred with DCM (5 mL) and water (1 mL) at 0° C. TFA (5 mL) was then added and the reaction stirred for 3 hours. After completion was shown on TLC with (Rf=0, ethyl acetate), the reaction was concentrated and co-evaporated with toluene 6 times. The mixture was dissolved in anhydrous anhydrous pyridine (1 mL) and acetic anhydride (1 mL) and stirred for 16 hours at RT. DCM was added and the organic layer was washed with $NaHCO_3$ (sat. aq.) until a neutral pH was reached and then washed with brine. The organic layer was dried over $Na_2SO_4$ and concentrated in vacuo, the compound was columned using flash chromatography to obtain compound 21 (1:0.5, α:β) in 81% yield over two steps (53 mg, 77 µmol). $^1$H NMR (600 MHz, CDCl$_3$): δ=7.76 ($J_{Ha, Hc}$=7.7 Hz, d, 2H, Ha, FMOC), 7.64 (m, 2H, Hb, FMOC), 7.40 ($J_{Hc, Ha}$=$J_{Hc, Hd}$=7.3 Hz, dd (apt), 2H, Hc, FMOC), 7.30 (m, 2H, Hd, FMOC), 6.06 (d, $J_{H1'α,H2'α}$=2.0 Hz, 1H, H1'α), 5.82 (bs, 1H, H1'β), 5.65 (NH), 5.51-5.44 (m, 2H, H4'α and H2β), 5.41 ($J_{H4'β,H3'β}$=$J_{H4'β,H2'β}$=9.9 Hz, dd (apt), 1H, H4'β), 5.32 (m, 1H, H3'α), 5.24 ($J_{H2'α,H1'α}$=2.2 Hz, $J_{H2'α,H3'α}$=3.3 Hz, dd, 1H, H2'α), 5.17-5.05 (m, 3H, H6'α, β and H3β), 4.42 ($J_{HfA',Hg}$=7.3 Hz, $J_{HfA',HfB}$=10.4 Hz, 1H, ABX, HfA), 4.32 ($J_{HfB,He'}$=7.1 Hz, $J_{HfB',HfA}$=10.0 Hz, 1H, ABX, HfB), 4.22 (m, 1H, He), 4.08 ($J_{H5'α, H4'α}$=9.9 Hz, $J_{H5'α,H6'α}$=2.6 Hz, dd, H5'α), 3.88-3.73 (m, 1H, H7'A, H5β), 3.62 (m, 1H, H7'B), 3.53 (m, 2H, CH$_2$CH$_2$NH), 3.41 (m, 2H, CH$_2$NH), 2.2-1.9 (CH$_3$). $^{13}$C NMR (150 MHz, CDCl$_3$) δ=171.4, 170.5, 170.4, 170.3, 170.2, 170.1, 169.8, 168.7, 168.4 (C(O)CH$_3$), 156.9 (OC(O)), 144.4, 144.3 (CH$_2$CHC×2), 141.6 (CH$_2$CHCC×2), 128.0 (CHc×2), 127.4 (CHd×2), 125.5 (CHb), 120.3 (CHa×2), 90.7 (C1'α), 90.8 (C1'), 74.8 (C5'β), 72.4 (C5'α), 71.1-70.7 (C3'β, C6'α, C6'β, CH$_2$CH$_2$NH), 69.3 (C3'α), 68.6 (C2'α), 68.5-68.1 (C7' and C2'β), 67.1 (Cf), 66.7 (C4'α), 66.6 (C4'β), 47.7 (He), 41.1 (CH$_2$NH), 21.3-20.8 (CH$_3$). HRMS m/z Calcd for C$_{34}$H$_{39}$NO$_{14}$Na [M+Na]$^+$ 708.2268, found 708.22804.

2,3,4,6-Tetra-O-acetyl-[7-O-(FMOC-aminoethyl)-D-glycero-3-D-manno-heptopyranosyl (22)

Compound 21 (52.7 mg, 77 µmol) was dissolved into DCM (200 µL) and to this was added acetic acid (100 µL) and HBR in acetic acid (500 µL) under a nitrogen atmosphere. The reaction was stirred for 16 hours at RT after which TLC monitoring showed that the reaction was to completion (Rf=0.7, diethylether). The mixture was then poured into iced water and extracted with DCM, washed with NaHCO$_3$ (sat. aqueous) and water. After this, the reaction mixture was diluted with DCM, washed with NaHCO$_3$ (sat. aq.) and water, dried with MgSO$_4$ and concentrated in vacuo. The bromide was dissolved in DCM (2 mL) and water was added (2 mL) as well as silver triflate (40 mg, 155 µmol) and silver carbonate (41 mg, 149 µmol). The bromide was hydrolyzed overnight, diluted with DCM and washed with water. The DCM layer was partitioned, dried with MgSO$_4$, filtered and concentrated in vacuo. Column chromatography afforded compound 22 in 56% yield (27.5 mg, 43 µmol). HRMS m/z Calcd for C$_{32}$H$_{37}$NO$_{13}$Na [M+Na]$^+$ 666.2163, found 666.2164.

Diphenyl (2,3,4,6-tetra-O-acetyl-[7-O-(FMOC-aminoethyl)-D-glycero-3-D-manno-heptopyranosyl) phosphate (23β)

Compound 22 (27.5 mg, 43 µmol) was coevaporated using toluene and dried under vacuum overnight. After 16 hours, 22 was dissolved in anhydrous DCM (1 mL) and DMAP (25.4 mg, 210 µmol) was added. Phosphoryl chloride (155 µL, 845 µmol) was also coevaporated with toluene and was dissolved into DCM (1 mL) and using a syringe pump, dropped at a rate of 0.5 mL/h over 2 hours under N$_2$, the reaction was to completion after 5 hours. The reaction was diluted with DCM and washed with TEAB buffer (until a basic pH was reached), water and brine. The organic layer was then dried with Na$_2$SO$_4$, filtered and concentrated under reduced pressure. Flash chromatography using hexane: diethyl ether gave title compound 23β in 28% yield (10.7 mg, 12 µmol, α:β, 3:2). $^1$H NMR, (600 MHz, CDCl$_3$) δ=7.76 ($J_{Ha, Hc}$=7.7 Hz, d, Ha, FMOC), 7.64 ($J_{Hb, Hd}$=7.3 Hz, d, Hb, FMOC), 7.40-7.27 (m, 10H, Hc and Hd FMOC and Ph), 7.24-7.15 (m, 4H, Ph), 5.76 (m, NH), 5.65 ($J_{H1',P}$=6.8 Hz, dd, 1H, H1'), 5.46 (m, 1H, H2'), 5.37 ($J_{H4',H}$=$J_{H4',H5'}$=9.3 Hz, dd (apt), 1H, H4'), 5.19 (m, 1H, H6'), 5.05 ($J_{H3', H2'}$=3.1 Hz, $J_{H3', H4'}$=8.6 Hz, dd, 1H, H3'), 4.42 ($J_{HfA,B',Hg}$=7.1 Hz, $J_{HfA',HfB}$=10.9 Hz, ABX, Hf), 4.21 ($J_{Hg',HfA}$=$J_{Hg',HfB'}$=7.1 Hz, ABX, Hg), 3.90 ($J_{H5', H6'}$=4.8 Hz, $J_{H5',H4'}$=9.1 Hz, dd, 1H, H5'), 3.69 ($J_{H7A',H6'}$=4.7 Hz, $J_{H7A',H7B}$=10.4 Hz, ABX, H7A'), 3.56 ($J_{H7B',H6'}$=5.5 Hz, $J_{H7B',H7A'}$=10.7 Hz, ABX, H7B'), 3.52 (m, ABX, 1H, CHACH$_2$NH), 3.43 (m, ABX, 1H, CHBCH$_2$NH), 3.38 (m, 2H, CH$_2$NH), 2.10, 2.09, 2.06, 1.97 (CH$_3$). $^{13}$C NMR (150 MHz, CDCl$_3$) δ=170.4, 170.1, 170.0 (C(O)CH$_3$), 157.0 (OC(O)), 150.7, 150.3 (CO,Ph×2), 144.4, 144.3 (CH$_2$CHC×2), 141.7 (CH$_2$CHCC×2), 130.3, 130.1 (CHOPh), 128.0 (CHc×2), 127.4 (CHd×2), 126.2, 126.1 (CHOPh), 125.6, 125.5 (CHb), 120.6, 120.5 (CHOPh), 120.3 (CHa×2), 95.2 ($^2J_{31P, C1}$=5.0 Hz, C1'), 74.2 (C5'), 70.8 (C6'), 70.6 (CH$_2$CH$_2$NH), 70.3 (C3'), 68.2 (C7'), 68.1 ($^3J_{31P, C2}$=9.2 Hz, C2'), 67.1 (Cf), 66.6 (C4'), 47.7 (He), 41.1 (CH$_2$NH), 21.3, 21.2, 20.9, 20.8 (CH$_3$). $J_{C1', H1'}$=170 Hz. $^{31}$P NMR (242 MHz, CDCl$_3$) δ −14.0. HRMS m/z Calcd for C$_{44}$H$_{46}$NO$_{1-6}$PNa [M+Na]$^+$ 898.2452, found 893.2485.

7-O-(Aminoethyl)-D-glycero-β-D-manno-heptopyranose phosphate (JS10a)

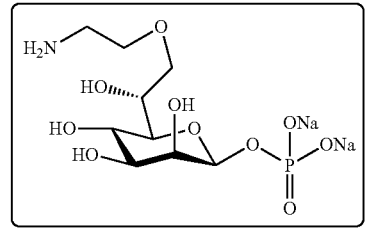

JS10a

Compound 23β (7.7 mg, 8.8 µmol) was stirred in anhydrous methanol at RT with PtO$_2$ under balloon pressure for 48 hours. When activated, the brown PtO$_2$ turns to black. After filtration over celite and concentration, the compound was dissolved into methanol:water:triethylamine (7:3:1, v:v:v) at a pH of 11 for 4 hours after which it was concentrated and freeze dried over water. Purification on a desalting column (G-10) and exchanging the triethylamine ions for sodium ions gave compound JS10a in 30% yield (0.9 mg, 2.6 µmol). $^1$H NMR, (600 MHz, D$_2$O) δ=5.05 ($J_{H1',P}$=8.7 Hz, d, 1H, H1'), 4.13 (m, 1H, H6'), 3.99 ($J_{H2',H3'}$=2.8 Hz, d, 1H, H2'), 3.87-3.73 (m, 4H, H7' and CH$_2$CH$_2$NH$_2$), 3.68 ($J_{H3',H2'}$=3.1 Hz, $J_{H3',H4'}$=9.7 Hz, dd, 1H, H3'), 3.65 ($J_{H4',H3'}$=$J_{H4α,H5'}$=9.8 Hz, dd (apt), 1H, H4'), 3.52 ($J_{H5',H6'}$=2.9 Hz, $J_{H5',H4'}$=9.6 Hz, dd, 1H, H5'), 3.21 ($J_{CH2,OCH2A}$=$J_{CH2,OCH2A}$=5 Hz, apt, 1H, CH$_2$NH$_2$). $^{13}$C NMR (from HSQC, D$_2$O) δ=93.3 (C1'), 77.2 (C5'), 72.8 (CH3'), 71.2 (C2'), 70.2 (C7'), 69.2 (C6'), 67.4 (C4'), 66.7 (CH$_2$CH$_2$NH), 38.9 (CH$_2$NH$_2$). MS m/z Calcd for C$_9$H$_{19}$NO$_{10}$P [M−H]$^−$ 332.0752, found 332.0758.

7-O-(Aminoethyl)-D-glycero-D-manno-heptopyranose (JS11a)

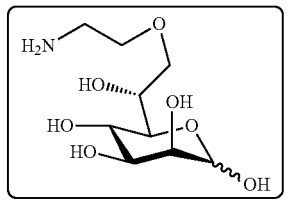
JS11a

Compound 19 (60.5 mg, 95 µmol) was treated with DCM, TFA and water (5:5:1, v:v:v). After 1 hour, the compound was concentrated and purified using reverse phase. The FMOC protected compound was then dissolved into DMF (800 µL) and piperidin (200 µL). After an hour, the compound was concentrated in vacuo and few drops of HCl (5 M) were added to the compound and it was desalted on a G-10 column. Pure JS11a was obtained in 51% overall yield (12.4 mg, 49.0 µmol). $^1$H NMR, (600 MHz, D$_2$O) δ=5.16 ($J_{H1'\alpha, H2'\alpha}$=1.7 Hz, d, 1H, H1'α), 4.87 ($J_{H1'\beta, H2'\beta}$=1.1 Hz, d, 1H, H1'β), 4.22-4.17 (m, 2H, H5'α and H5'β), 3.94 ($J_{H2'\beta, H3'\beta}$=3.2 Hz, $J_{H2'\beta, H1'\beta}$=1.0 Hz, d, 1H, H2'β), 3.92 ($J_{H2'\alpha, H3'\alpha}$=3.3 Hz, $J_{H2'\alpha, H1\alpha}$=2.0 Hz, dd, 1H, H2'α), 3.90 ($J_{H5'\alpha, H6'\alpha}$=3.0 Hz, $J_{H5'\alpha, H4\alpha}$=9.6 Hz, dd, 1H, H5'α), 3.84-3.77 (m, 5H, H3'α, H7A', C$\underline{H}_2$CH$_2$NH$_2$), 3.75 ($J_{H4'\alpha, H3'\alpha}$ =$J_{H4'\alpha, H5'\alpha}$=9.7 Hz, dd (apt), 1H, H4'α), 3.73-3.67 (H7B', H4'β), 3.64 ($J_{H4'\beta, H3'\beta}$=3.2 $J_{H4'\beta, H5'\beta}$=9.4 Hz, dd (apt), 1H, H4'β), 3.46 ($J_{H5'\beta, H6'\beta}$=3.0 Hz, $J_{H5'\beta, H4'\beta}$=9.5 Hz, dd, 1H, H5'β), 3.24 ($J_{CH2, OCH2A}$=$J_{CH2, OCH2B}$=5.4 Hz, apt, 1H, C$\underline{H}_2$NH$_2$). $^{13}$C NMR (600 MHz, D$_2$O) δ=94.0 (C1'α), 93.8 (C1'β), 76.6 (C5'β), 73.2 (C3'β), 72.6 (C5'α), 71.0 (C3'β and C7'α), 70.7 (C7'β), 70.5 (C2'α and C3'α), 70.0 (C6'α), 69.8 (C6'β), 67.4 (C4'α), 67.2 (C4'β), 66.6 (C$\underline{H}_2$CH$_2$NH), 38.2 (C$\underline{H}_2$NH$_2$). HRMS m/z Calcd for C$_9$H$_{19}$NO$_7$Na [M+Na]$^+$ 276.1059, found 276.1068.

D-glycero-D-manno-heptopyranose (JS12a)

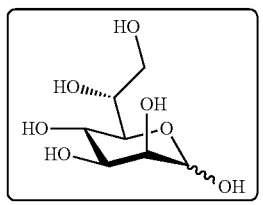
JS12a

JS12a was synthesized as described by Brimacombe et al. [9, 10]

pH-Rhodo-7-O-(aminoethyl)-D-glycero-β-D-manno-heptopyranose phosphate (JS13a)

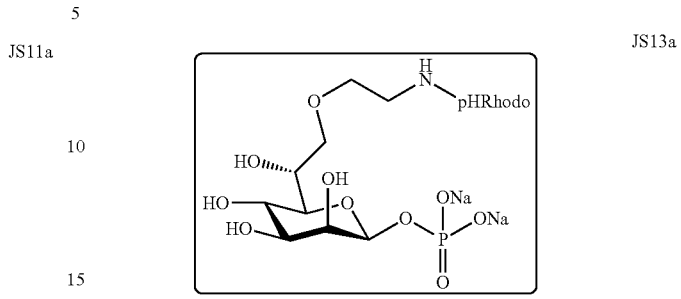
JS13a

JS10a (700 µg) was dissolved in PBS×1 (100 µL) and pH-Rhodo activated ester (1 mg in 100 µL DMSO) was added to the mixture. After 24 hours, the DMSO the mixture was concentrated in vacuo and JS12a was purified using reverse phase. LRMS and HPLC showed that JS13a was only present at a ratio of 6% in the mixture and was tested according to this. $^1$H NMR, (500 MHz, D$_2$O) δ=7.39, 7.30, 7.28, 7.09, 7.02, 6.90, 6.88, 6.48, 5.06, 5.04, 4.18, 4.17, 4.16, 4.00, 3.86, 3.73, 3.70, 3.69, 3.68, 3.67, 3.66, 3.64, 3.42, 3.36, 3.35, 3.15, 2.73, 2.68, 2.35, 2.34, 2.32, 2.01, 1.92, 1.85, 1.83, 1.49, 4.48, 1.41, 1.38, 1.36, 1.34, 1.30, 1.29, 1.27, 1.26, 1.22, 1.13, 1.12, 1.10, 0.88. LRMS m/z Calcd for C$_{41}$H$_{60}$N$_5$O$_{13}$P [M+H]$^+$ 861.39, found 861.55.

Biotin-7-O-(aminoethyl)-D-glycero-(3-D-manno-heptopyranose phosphate (JS14a)

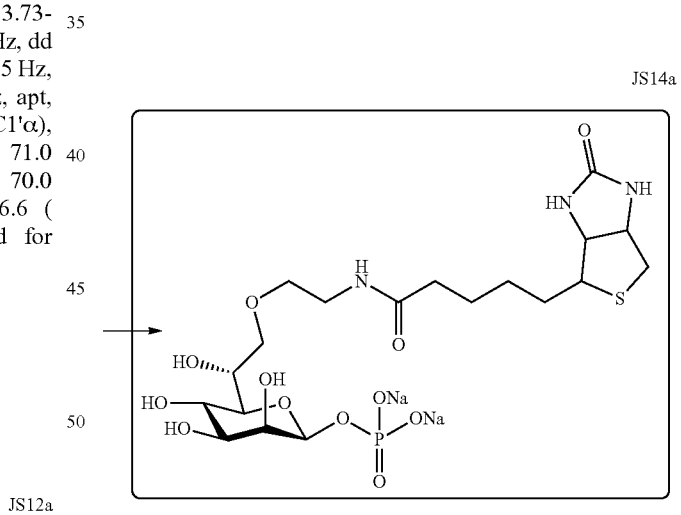
JS14a

JS10a (7.2 mg, 21 µmol) was dissolved in water (1 mL) and (+)-Biotin N-hydroxysuccinimide ester (22 mg, 64 µmol in 600 µL DMF) was added to the mixture as well as one drop of Et$_3$N. After 24 hours, the reaction was completed (TLC, rf=0.32. 5:7:2:2, CHCl$_3$:MeOH:Water:NH$_4$OH). Water was added and the water layer was washed three times with ethyl acetate. After the water layer was concentrated and dissolved in brine. This solution was purified on a G-10 column to obtain 2.5 mg (4.5 µmol) of JS14a in 21% yield. $^1$H NMR, (500 MHz, D$_2$O) δ=5.11 ($J_{H1', P}$=9.0 Hz, d, 1H, H1'), 4.62 (m, 1H, C$\underline{H}$CH$_2$S), 4.43 (m, 1H, C$\underline{H}$CHS), 4.17 (m, 1H, H6'), 4.00 (m, 1H, H2'), 3.79 (m, 1H, H7'A), 3.74-3.62 (m, 6H, H7'B, C$\underline{H}_2$CH$_2$NH$_2$, H3', H4'), 3.49 (m, 1H, H5'), 3.41 (m, 1H, C$\underline{H}_2$NH$_2$), 3.35 (m, 1H, C$\underline{H}$S), 3.01 (J$_{HA, CHNH}$=4.8 Hz, J$_{HA,HB}$=13.1 Hz, ABX, 1H, C$\underline{H}$AHBS), 2.79 (J$_{HB, CHNH}$=3.6 Hz, J$_{HB,HA}$=15.0 Hz, ABX, 1H, CHA H$\underline{B}$S), 2.29 (J$_{CH2C(O), CH2CH2C(O)}$=7.3 Hz, 2H, C$\underline{H}_2$C(O)), 1.8-1.5 (m, 4H, C$\underline{H}_2$CH$_2$C(O) and C$\underline{H}_2$CHS), 1.40 (m, 2H, C$\underline{H}_2$CH$_2$CH$_2$C(O)). $^{13}$C NMR (100 MHz, D$_2$O) δ=177.1 ($\underline{C}$(O)CH$_2$), 95.6 ($^2$J$_{31P, C1'}$=4.4 Hz, d, C1'), 77.4 (C5'), 72.7 (C3'), 70.9 ($^3$J$_{31P, C2'}$,=6.8 Hz, d, C2'), 70.6 (C7'), 69.9 (C6'), 69.3 ($\underline{C}$H$_2$CH$_2$NH$_2$), 66.9 (C4'), 62.2 ($\underline{C}$HCHS), 60.4 ($\underline{C}$HCH$_2$S), 55.4 ($\underline{C}$HS), 39.7 ($\underline{C}$H$_2$S), 39.0 ($\underline{C}$H$_2$NH$_2$), 35.5 ($\underline{C}$H$_2$C(O)), 27.9 ($\underline{C}$H$_2$CH$_2$CH$_2$C(O)), 27.7 ($\underline{C}$H$_2$CHS), 25.1 ($\underline{C}$H$_2$CH$_2$C(O)). LRMS m/z Calc'd for C$_{19}$H$_{35}$N$_3$O$_{12}$PS [M+H]$^+$, 560.1679, found 560.31.

Biotin-PEG4-7-O-(aminoethyl)-D-glycero-β-D-manno-heptopyranose phosphate (JS24a)

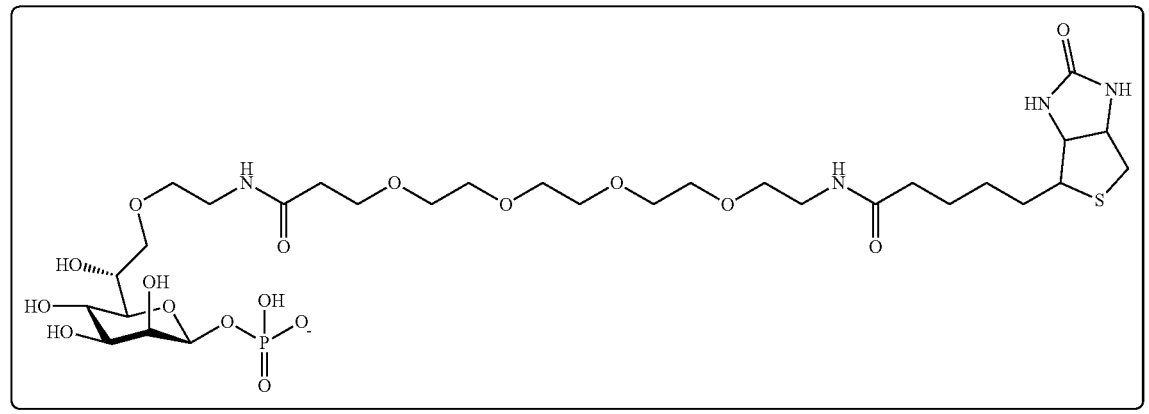

JS24a

JS10a (4.1 mg, 12 μmol) was dissolved in water (1 mL) and Biotin-dPEG4-TFP ester (35 mg, 55 μmol in 200 μL DMF) was added to the mixture. After 24 hours, the reaction was not completed. At this point, 100 μL of sat. NaHCO3 was added and after 3 hours the reaction was shown to be completed (TLC, rf=0.32. 5:7:2:2, CHCl$_3$:MeOH:Water: NH4OH). The solvents were then evaporated, and the reaction mixture purified on a Biogel P-2 column. 4.8 mg (5.9 μmol) of JS24a was obtained with 50% yield. 1H NMR, (600 MHz, D2O) δ=5.05, 4.62, 4.44, 4.14, 4.00, 3.79, 3.69, 3.48, 3.40, 3.34, 3.00, 2.78, 2.57, 2.30, 1.65, 1.41 LRMS m/z Calc'd for C30H54N4O17PS [M+H]+, 805.29, found 805.19.

Fluorescein-7-O-(aminoethyl)-D-glycero-β-D-manno-heptopyranose phosphate (JS25a)

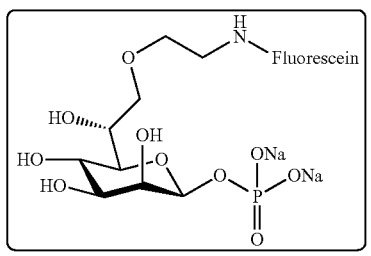

JS25a

JS10a (1.5 mg, 4.5 μmol) was dissolved in water (1 mL) and fluorescein N-hydroxysuccinimide ester (5 mg, 8.5 μmol in 200 μL DMF) was added to the mixture. After 24 hours, the reaction did not seem to completion and 100 μL of sat. NaHCO3 was added. Then after 3 hours, the reaction was completed (TLC, rf=0.50. 5:7:2:2, CHCl$_3$:MeOH:Water: NH4OH). The DMF and water was then evaporated on a Genevac personal evaporator. The compound was then purified on a biogel P-2 column to obtain 1.6 mg (2.2 μmol) of JS25a in 40% yield. $^1$H NMR, (600 MHz, D2O) δ=8.26, 8.00, 7.62, 7.45, 7.26, 6.90, 6.82, 5.13, 4.17, 4.11, 4.00, 3.77, 3.66, 3.54, 3.47, 3.39, 3.32, 3.28, 2.92, 2.32, 2.24, 1.69, 1.61, 1.44, 1.34. LRMS m/z Calc'd for C36H40N2O17P [M–H]–, 803.69, found 803.17.

Example 2: In Vitro Biological Testing

Immunomodulatory activity was illustrated for compounds JS10a, JS13a, JS14a, JS24a and JS25a according to the data obtained from the experiments highlighted by FIGS. 9-17.

Figure 9A:
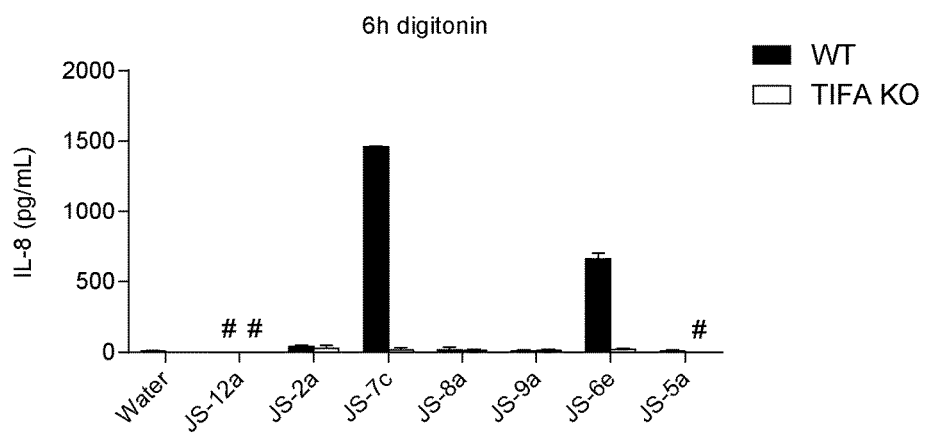
FIGS. 9A-B. Inflammatory response of human colonic epithelial cells (HCT 116) exposed to chemically synthesized analogues. Wild type (WT) or TIFA knockout (TIFA KO) cells were treated with compounds in the presence of digitonin for 20 min, treatment was removed, cells were washed and then cultured in normal medium without the synthetic compounds for 6 hr before IL-8 levels in culture supernatants were measured by ELISA. (A) Cells were treated with water or 10 μg/mL of the indicated compound. Data are means±standard error mean of technical triplicates. (B) Cells were treated with the NOD1 agonist C12-iE-DAP (39.8 μM) or with two different molar concentrations of compounds (30 μM or 150 μM). Two batches of dd-β-HBP and dd-β-HMP synthesized independently of one another were tested (batch #1 and batch #2) to assess consistency of the chemical synthesis. Data are means±standard error mean of two (150 μM treatment) or three (all other treatments) independent experiments. Nod1 agonist: C12-iE-DAP (20 μg/ml, 39.8 μM); JS-12: D-glycero-D-manno-heptose; JS-2: D-glycero-D-manno-heptose 7-phosphate; JS-7:D-glycero-β-D-manno-heptose-phosphate; JS-8: d-glycero-α-d-manno-heptose-phosphate; JS-9: β-d-mannose phosphate; JS-6:d-glycero-β-d-manno heptose 1,7-biphosphate; JS-5: d-glycero-α-d-manno heptose 1,7-biphosphate.
Figure 9B:
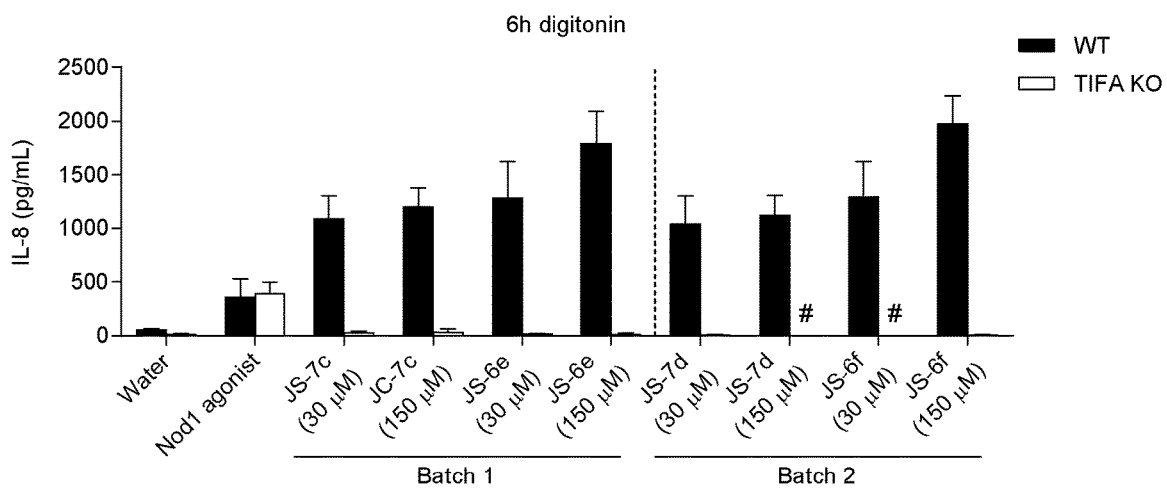

The data presented in FIG. 9 show that chemically synthesized DD-β-HMP (JS7) elicits an inflammatory response similar to that apparent with DD-β-HBP (JS6) when administered to human colonic epithelial cells (HCT 116). The relative absence of activity in cells that lack TIFA (TIFA KO) demonstrates that the activity of both compounds is TIFA-dependent.

Figure 10A:
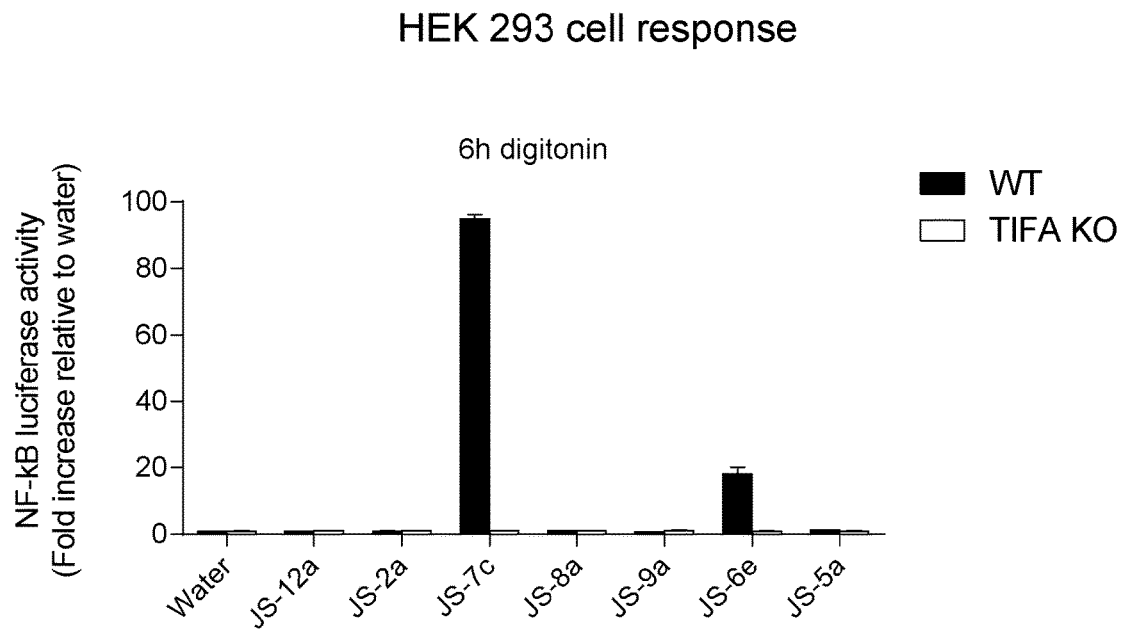
FIGS. 10A-B. Effect of chemically synthesised analogues on human embryonic kidney cells (HEK 293T) encoding an NF-κB-driven luciferase reporter gene. NF-κB luciferase activity was measured in wild type (WT) or TIFA knockout (TIFA KO) cells treated with compounds in the presence of digitonin for 20 min, washed, and then cultured in normal medium without the synthetic compounds for 6 hrs after treatment, before luciferase activity was measured. (A) Cells were treated with 10 μg/mL of the indicated compound. Data are means±standard error mean of technical triplicates. (B) Cells were treated with two different molar concentrations of compound (30 μM or 150 μM). Two batches of DD-β-HBP and DD-β-HMP synthesized independently of one another were tested (batch #1 and batch #2) to assess consistency of the chemical synthesis. Data are means±standard error mean of technical triplicates and are representative of three independent experiments. JS-12: D-glycero-D-manno-heptose; JS-2: D-glycero-D-manno-heptose 7-phosphate; JS-7:D-glycero-β-D-manno-heptose-phosphate; JS-8: D-glycero-α-D-manno-heptose-phosphate; JS-9: β-D-mannose phosphate; JS-6:D-glycero-β-D-manno heptose 1,7-biphosphate; JS-5: D-glycero-α-D-manno heptose 1,7-biphosphate.
Figure 10B:
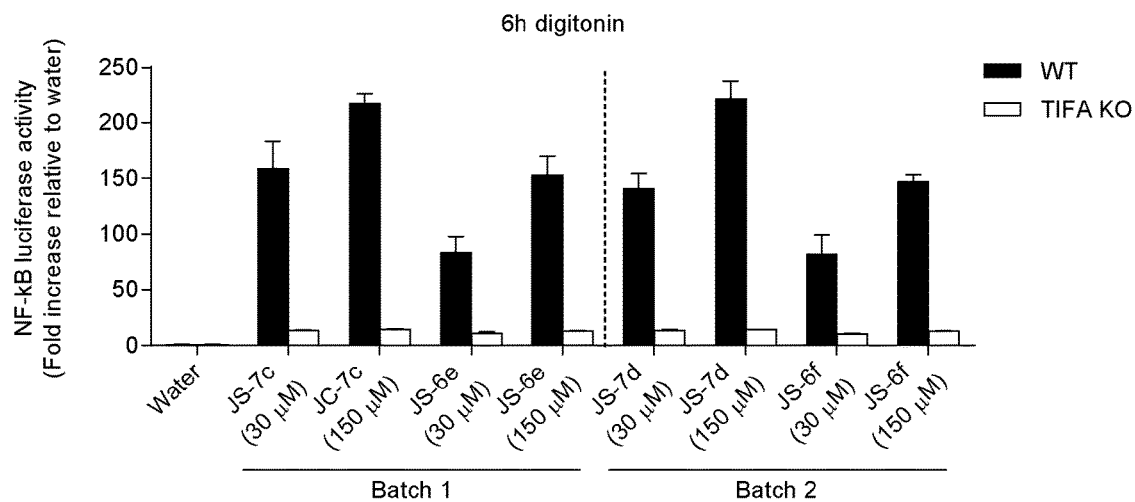

The data presented in FIG. 10 shows that chemically synthesized DD-β-HMP (JS7) elicits an inflammatory NF-κB response similar to that apparent with DD-β-HBP (JS6) when administered to human embryonic kidney cells (HEK 293). The relative absence of activity in cells that lack TIFA (TIFA KO) demonstrates that the activity of both compounds is TIFA-dependent.

Figure 11:
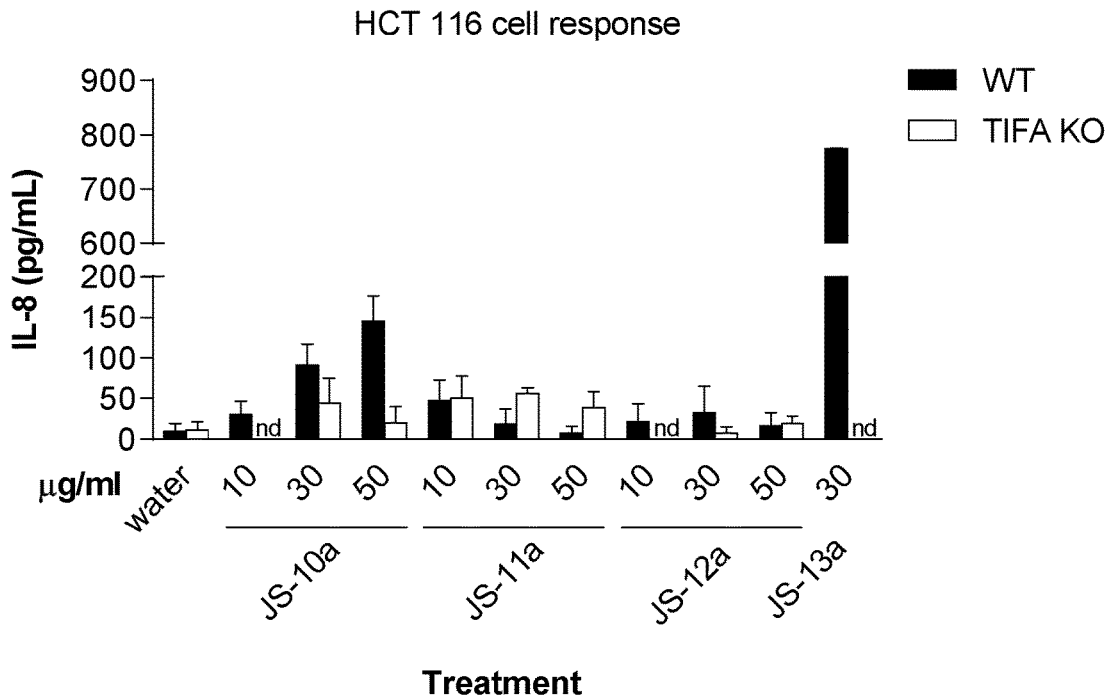
FIG. 11. Stimulation of human colonic epithelial cells by compounds/products according to the invention. Human colonic epithelial cells (HCT 116) that were either wild type (WT) or deficient in TIFA protein expression (knockout, KO) were stimulated for 20 minutes in permeabilization buffer (5 μg/mL digitonin) in the presence of water or 10 μg/mL, 30 μg/mL, or 50 μg/mL of indicated synthetic compounds according to the invention. Treatment was removed, cells were washed, and cells were incubated for 6 hours in complete media before IL-8 levels in culture supernatants was measured by ELISA. The results are the mean±standard error of the mean of three technical replicates. JS-10: 7-O-(Aminoethyl)-D-glycero-β-D-manno-heptopyranose phosphate; JS-11: 7-O-(Aminoethyl) -D-glycero-D-manno-heptopyranose; JS-12: D-glycero-D-manno-heptose; Js-13: pH-Rhodo -7-O-(aminoethyl)-D-glycero-β-D-manno-heptopyranose phosphate.

The data presented in FIG. 11 show that JS-10a elicits a modest inflammatory response whereas JS-13a elicits a strong inflammatory response when administered to human colonic epithelial cells (HCT 116). The relative absence of activity in TIFA KO cells demonstrates that the activity of both compounds is TIFA-dependent.

Figure 12:
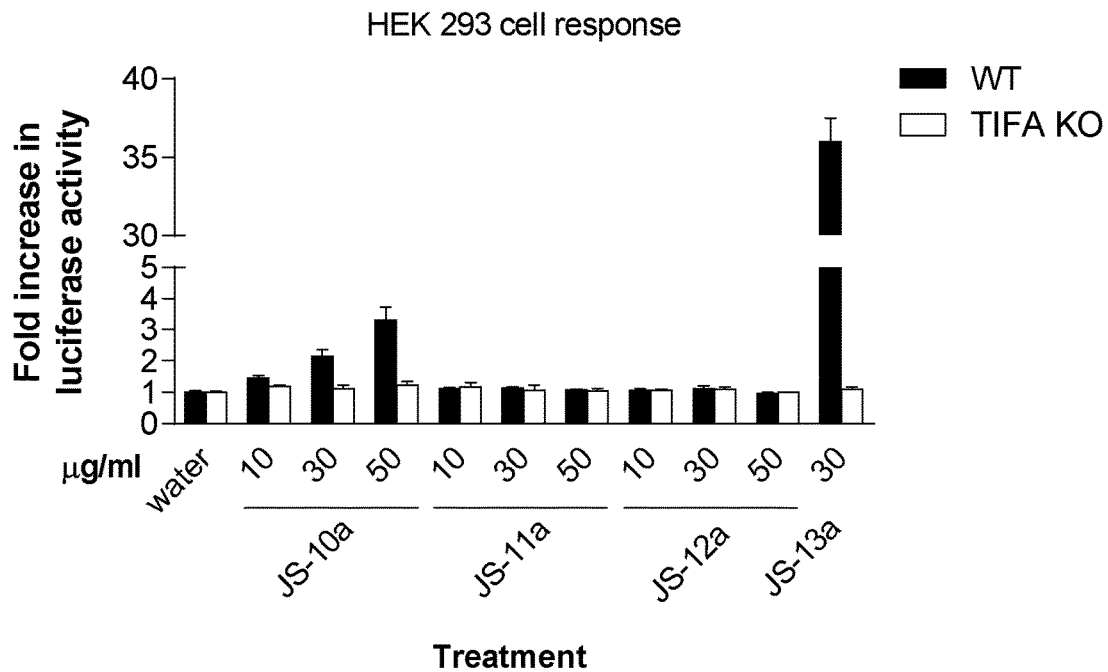
FIG. 12. Effects of compounds/products according to the invention on HEK 293T cells encoding an NF-κB-driven luciferase reporter gene. HEK 293T cells were transfected with a plasmid encoding an NF-κB-driven luciferase reporter. After 24 hours, cells were stimulated for 20 minutes in permeabilization buffer (5 μg/mL digitonin) in the presence of water or 10 μg/mL, 30 μg/mL, or 50 μg/mL of indicated synthetic compounds according to the invention. Treatment was removed; cells were washed and incubated for 6 hours incomplete medium. A luciferase assay was then performed. JS-12a control: D-glycero-D-manno heptose. The results are the means±standard error of the mean of three technical replicates. JS-10: 7-O-(Aminoethyl)-D-glycero-β-D-manno-heptopyranose phosphate; JS-11: 7-O-(Aminoethyl)-D-glycero-D-manno-heptopyranose; JS-12: D-glycero-D-manno-heptose; Js-13: pH-Rhodo-7-O-(aminoethyl)-D-glycero-β-D-manno-heptopyranose phosphate.

The data presented in FIG. 12 show that JS-10a elicits a modest inflammatory response whereas JS-13a elicits a strong inflammatory response when administered to human embryonic kidney cells (HEK 293). The relative absence of activity in TIFA KO cells demonstrates that the activity of both compounds is TIFA-dependent.

Figure 13:
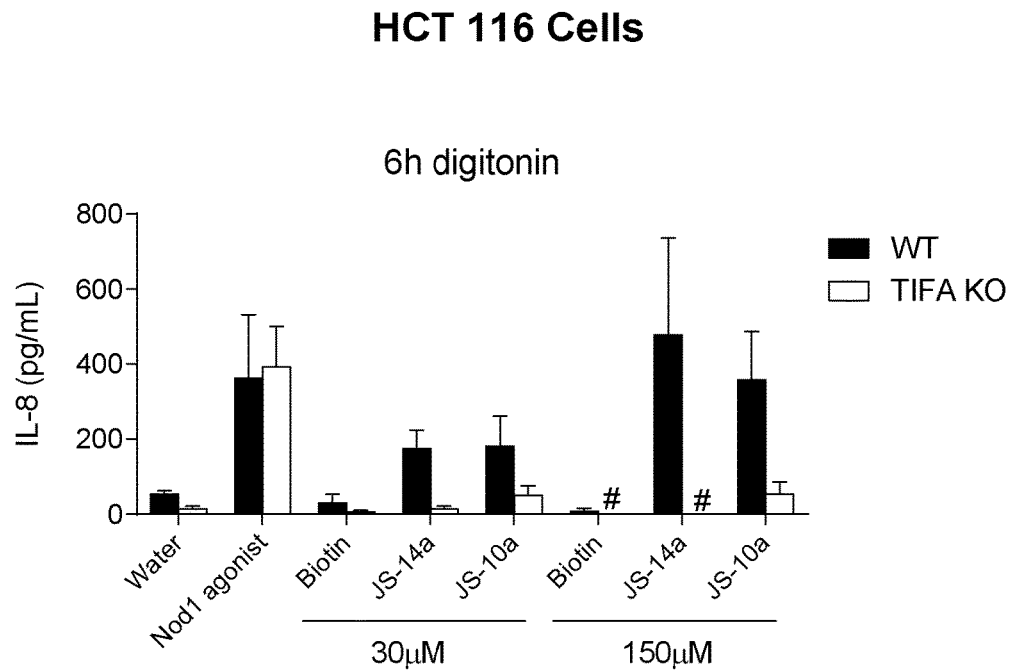
FIG. 13. Stimulation of human colonic epithelial cells by compounds/products according to the invention. Human colonic epithelial cells (HCT 116) that were either wild type (WT) or deficient in TIFA protein expression (knockout, TIFA KO) were stimulated for 20 minutes in permeabilization buffer (5 μg/mL digitonin) in the presence of water, 20 μg/mL of the Nod1 agonist C12-iE-DAP (39.8 μM, which induces inflammation in a TIFA-independent manner) or 30 μM or 150 μM of synthetic compound according to the invention. Treatment was removed, cells were washed, and cells were incubated for 6 hours in complete media before IL-8 levels in culture supernatants were measured by ELISA. The results are the mean±standard error of the mean of two (150 μM treatment) or three (all other treatments) independent experiments. #=none detected, JS-10: 7-O-(Aminoethyl)-d-glycero-β-d-manno-heptopyranose phosphate; JS-14: Biotin-7-O-(aminoethyl)-d-glycero-β-d-manno-heptopyranose phosphate, Nod1 agonist: C12-iE-DAP (20 μg/ml, 39.8 μM).

The data presented in FIG. 13 indicate that JS-10a and JS-14a activate similar inflammatory responses when administered to HCT 116 colonic epithelial cells. The relative absence of activity in TIFA KO cells indicate that this activity is TIFA-dependent. The Nod1 agonist activates a similar response but it is not TIFA-dependent.

Figure 14:
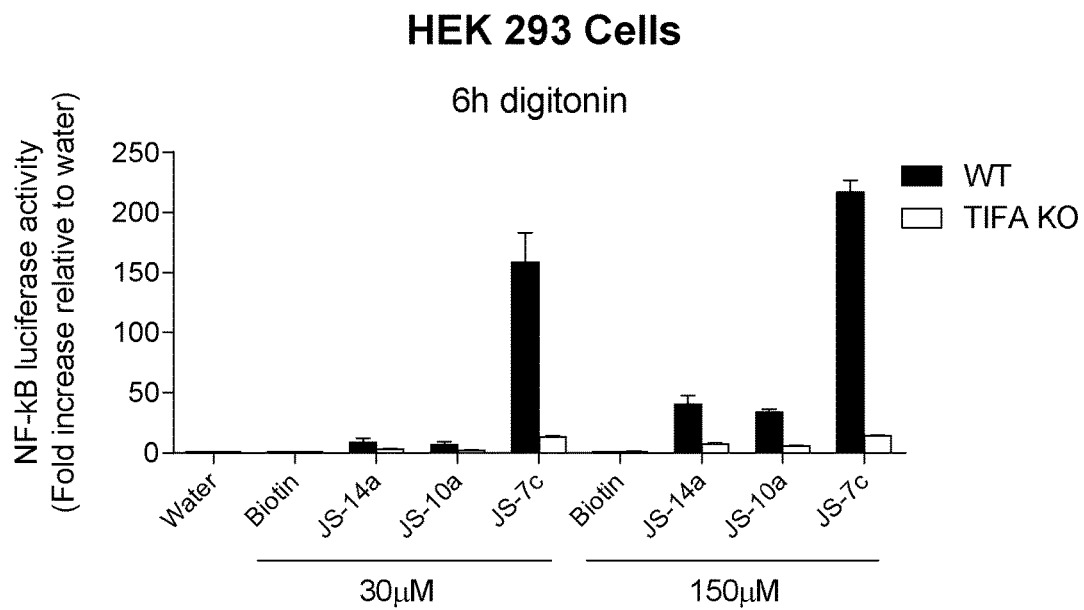
FIG. 14. Effects of compounds/products according to the invention on HEK 293T cells encoding an NF-κB-driven luciferase reporter gene. HEK 293T cells were transfected with a plasmid encoding an NF-κB-driven luciferase reporter. After 24 hours, cells were stimulated for 20 minutes in permeabilization buffer (5 μg/mL digitonin) in the presence of water, or either 30 μM or 150 μM of indicated synthetic compounds according to the invention. Treatment was removed; cells were washed and incubated for 6 hours in complete medium. A luciferase assay was then performed. The results are the mean and standard error of the mean of three technical replicates and are representative of three independent experiments. JS-7: JS-7:D-glycero-β-D-manno-heptose-phosphate; JS-10: 7-O-(Aminoethyl)-D-glycero-β-D-manno-heptopyranose phosphate; JS-14: Biotin-7-O-(aminoethyl) -D-glycero-β-D-manno-heptopyranose phosphate.

The data presented in FIG. 14 indicate that JS-10a and JS-14a activate similar NF-κB responses when administered to HEK 293 human embryonic kidney cells encoding an NF-κB-driven luciferase reporter. The relative absence of activity in TIFA KO cells indicate that this activity is TIFA-dependent. HMP (JS7) is included for comparison of the mono-phosphate with and without a linker at the 7-position.

Figure 15:
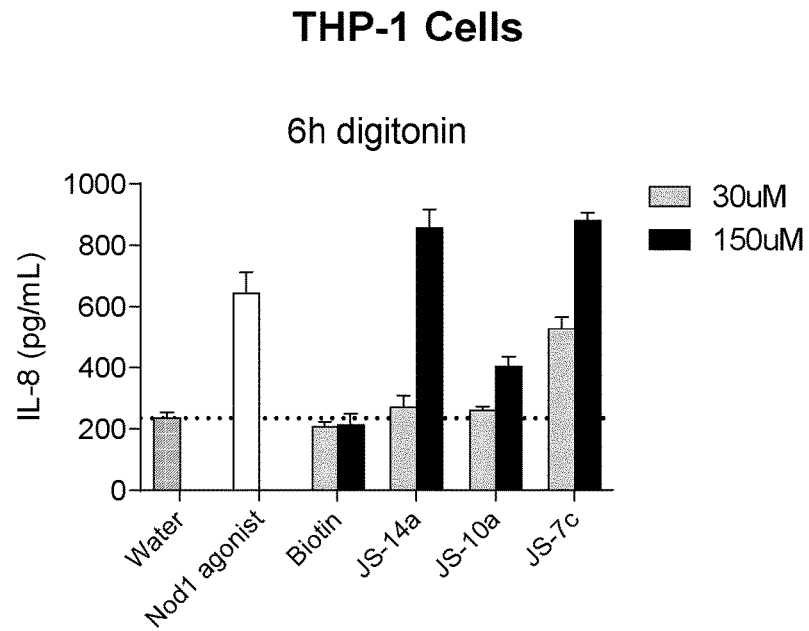
FIG. 15. Stimulation of human macrophages by compounds/products according to the invention. Human macrophage cells (THP-1) were stimulated for 20 minutes in permeabilization buffer (5 μg/mL digitonin) in the presence of water, 39.8 μM of the Nod1 agonist C12-iE-DAP (which stimulates in a TIFA-independent manner), or either 30 μM or 150 μM of synthetic compound according to the invention. Treatment was removed, cells were washed, and cells were incubated for 6 hours in complete media before the IL-8 levels in culture supernatants were measured by ELISA. The results are the mean and standard error of the mean of three technical replicates. Nod1 agonist: C12-iE-DAP (20 μg/ml, 39.8 μM); JS-7: JS-7:D-glycero-β-D-manno-heptose-phosphate; JS-10: 7-O-(Aminoethyl)-D-glycero-β-D-manno-heptopyranose phosphate; JS-14: Biotin-7-O-(aminoethyl)-D-glycero-β-D-manno-heptopyranose phosphate.

The data presented in FIG. 15 indicate that JS-10a and JS-14a both stimulate an inflammatory response when higher (150 μM) concentrations are administered to THP-1 human monocytes. HMP (JS7) is included for comparison of the mono-phosphate with and without a linker at the 7-position.

Figure 16:
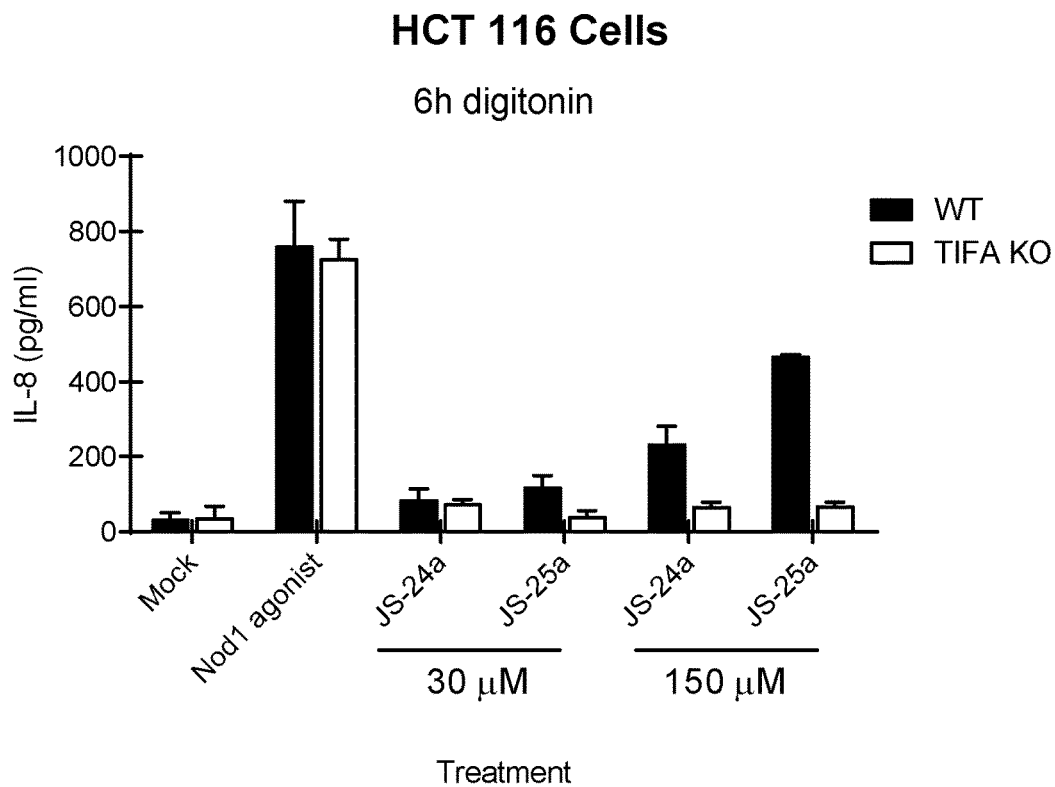
FIG. 16. Stimulation of human colonic epithelial cells by compounds/products according to the invention. Human colonic epithelial cells (HCT 116) that were either wild type (WT) or deficient in TIFA protein expression (knockout, TIFA KO) were stimulated for 20 minutes in permeabilization buffer (5 μg/mL digitonin) in the presence of water, 20 μg/mL of the Nod1 agonist C12-iE-DAP (39.8 μM, which induces inflammation in a TIFA-independent manner) or 30 μM or 150 μM of synthetic compound according to the invention. Treatment was removed, cells were washed, and cells were incubated for 6 hours in complete media before IL-8 levels in culture supernatants were measured by ELISA. The results are the mean±standard error of three technical replicates. JS-24a: 7-O-([Biotin]-dPEG4-amidoethyl)-D-Glycero-β-D-manno-heptopyranosyl phosphate; JS-25a: 7-O-([Fluorescein]-amidoethyl)-D-Glycero-β-D-manno-heptopyranosyl phosphate, Nod1 agonist: C12-iE-DAP (20 μg/ml, 39.8 μM).

The data presented in FIG. 16 indicate that JS-24a and JS-25a activate similar inflammatory responses when administered to HCT 116 colonic epithelial cells. The relative absence of activity in TIFA KO cells indicate that this activity is TIFA-dependent. The Nod1 agonist activates a similar response but it is not TIFA-dependent.

Figure 17:
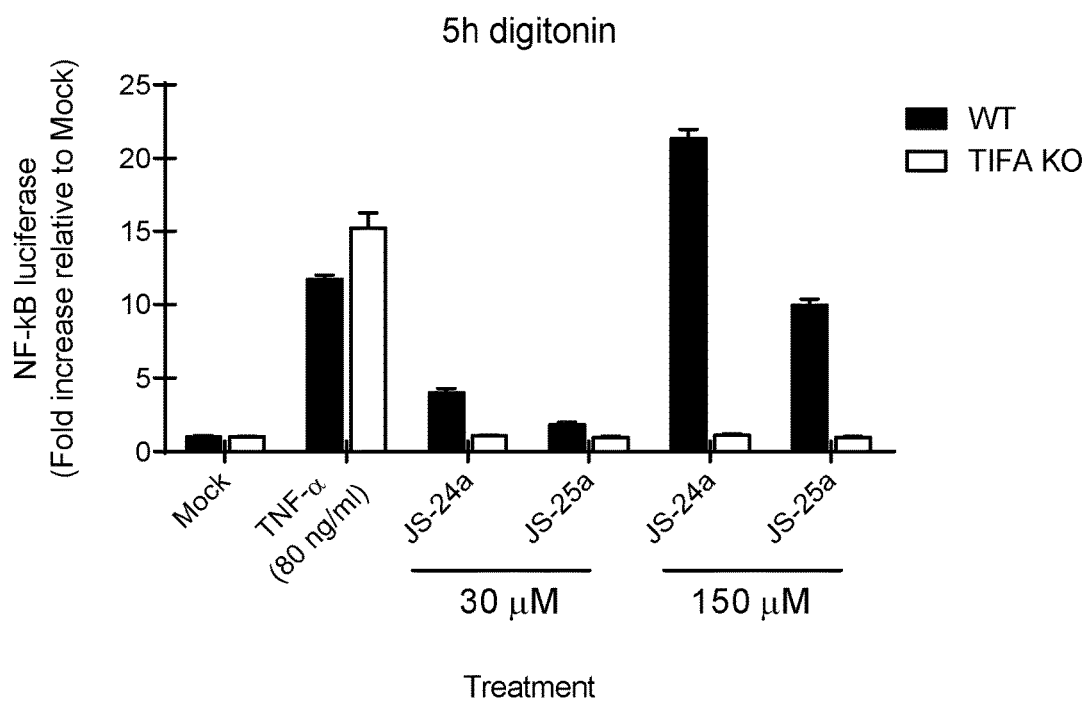
FIG. 17. Effects of compounds/products according to the invention on HEK 293T cells encoding an NF-κB-driven luciferase reporter gene. HEK 293T cells were transfected with a plasmid encoding an NF-κB-driven luciferase reporter. After 24 hours, cells were stimulated for 20 minutes in permeabilization buffer (5 μg/mL digitonin) in the presence of water, TNF-α (80 ng/mL) or either 30 μM or 150 μM of indicated synthetic compounds according to the invention. Treatment was removed; cells were washed and incubated for 5 hours in complete medium. A luciferase assay was then performed. The results are the mean±standard error of three technical replicates. JS-24a: 7-O-([Biotin]-dPEG4-amidoethyl)-D-Glycero-β-D-manno-heptopyranosyl phosphate; JS-25a: 7-O-([Fluorescein]-amidoethyl)-D-Glycero-β-D-manno-heptopyranosyl phosphate.

The data presented in FIG. 17 indicate that JS-24a and JS-25a activate similar NF-κB responses when administered to HEK 293 human embryonic kidney cells encoding an NF-κB-driven luciferase reporter. The relative absence of activity in TIFA KO cells indicate that this activity is TIFA-dependent.

Example 3: Additional HMP-Linkers

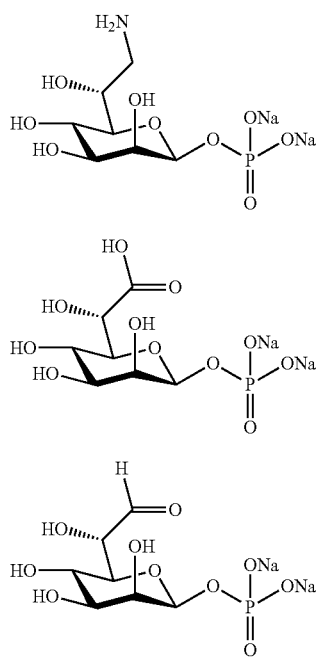

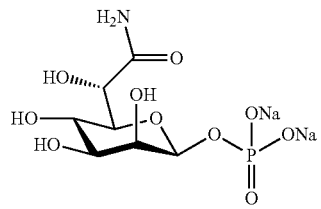

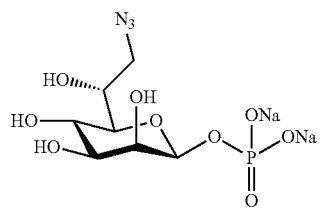

Additional compounds (JS 15 to JS19) can be synthesized according to standard techniques such as those described in Li et al., Carbohydrate Research, 2016, 432, 71-75 and Li et al. Organic letters, 2014, 16, 5628-5631.

For example, other compounds of formula (I) or (Ia):

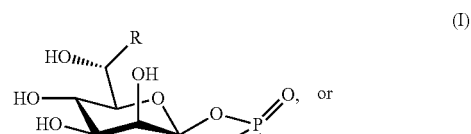

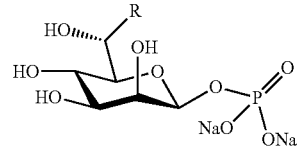

can be synthesized, where the R group may be any linkage moiety for conjugating with a molecule, and the resulting conjugate compound is capable of targeting and/or modulating an immune response thereof.

Particularly, the R group can be selected from the group consisting of: —C(O)OH, —C(O)H, —$C_{0-6}$alkyl-C(O)—$C_{1-6}$ alkyl, —$C_{0-6}$alkyl-$N_3$, —$C_{1-6}$ alkyl, —$C_{0-6}$alkyl—O—$C_{1-6}$ alkyl, —$C_{0-6}$alkyl-aryl, —$C_{0-6}$alkyl-O-aryl, —$C_{0-6}$alkyl-$C_{2-6}$-allyl groups, and —$C_{0-6}$alkyl-O—$C_{2-6}$-allyl, wherein said —$C_{0-6}$alkyl-C(O)—$C_{1-6}$ alkyl, —$C_{1-6}$ alkyl, $C_{0-6}$alkyl-O—$C_{1-6}$ alkoxy, -aryl, $C_{0-6}$alkyl-O-aryl, $C_{0-6}$alkyl-$C_{2-6}$-allyl groups, and $C_{0-6}$alkyl-O—$C_{2-6}$-allyl is optionally substituted with a: amino, acyloxy, alkoxy, carboxyl, carbalkoxyl, hydroxy, trifluoromethyl, cyano, nitro, acyl, or a halo group;

or R is selected from the group consisting of: $CH_2PO_3C(O)$—$C_{1-6}$ alkyl, $CH_2OPO_3C_{1-6}$ alkyl, $CH_2OPO_3$—$C_{1-6}$—O alkoxy, $CH_2OPO_3$-aryl, $CH_2OPO_3$—$C_{2-6}$-allyl, wherein said $CH_2OPO_3C(O)$—$C_{1-6}$ alkyl, $CH_2OPO_3C_{1-6}$ alkyl, $CH_2OPO_3$—$C_{1-6}$—O alkoxy, $CH_2PO_3$-aryl, $CH_2OPO_3$—$C_{2-6}$-allyl group is optionally substituted with a: amino, acyloxy, alkoxy, carboxyl, carbalkoxyl, hydroxy, trifluoromethyl, cyano, nitro, acyl, or a halo group.

More particularly, the R group can be selected from the group consisting of: —$CH_2$—$NH_2$; —C(O)OH; —C(O)H; —$N_3$; -lower alkyl or —O-lower alkyl groups containing 1-6 saturated or unsaturated carbon atoms; and -aryl, —O-aryl, —O-allyl or -allyl groups having 2-6 carbon atoms; wherein such alkyl, —O-alkyl, aryl, —O-aryl, -allyl or —O-allyl groups may be unsubstituted or may be substituted with: halo, hydroxy, trifluoromethyl, cyano, nitro, acyl, acyloxy, alkoxy, carboxyl, carbalkoxyl, or amino groups; or with a hydroxy, an amino or a halo group.

Additionally, it is possible to modify HMP via a phosphate residue, wherein R is $COPO_3C(O)$—$C_{1-6}$ alkyl, —$COPO_3C_{1-6}$ alkyl, —$COPO_3$—$C_{1-6}$—O alkoxy, —$COPO_3$-aryl, —$COPO_3$-aryl, —$COPO_3$—$C_{2-6}$-allyl. More particularly, the compounds of formula (I) as defined herein can be synthesized according to standard techniques, particularly according to U.S. Pat. No. 5,856,462.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications and patent applications cited in this specification are herein incorporated by reference as if each individual publication or patent application were specifically and individually indicated to be incorporated by reference in their entirety.

REFERENCES

1. Gaudet, R. G.; Sintsova, A.; Buckwalter, C. M.; Leung, N.; Cochrane, A.; Li, J.; Cox, A. D.; Moffat, J.; Gray-Owen, S. D. *Science*, 2015, 384, 1251-1255.
2. Gaudet, R. G.; Gray-Owen, S. D. *PLOS Pathog.* 2016, 12(9): e1005807.
3. Malott, R. J.; O. Keller, B.; Gaudet, R. G.; McCaw, S. E.; Lai, C. C. L.; Dobson-Belaire, W. N.; Hobbs, J. L.; St. Michael, F.; Cox, A. D.; Moraes, T. F.; Gray-Owen, S. D. *Proc. Natl. Acad. Sci.*, 2013, 110, 10234-10239.
4. Milivojevic, M.; Dangeard, A. S.; Kasper, C. A.; Tschon, T.; Emmenlauer, M.; Pique, C.; Schnupf, P.; Guignot, J.; Arrieumerlou, C. *PLOS Pathog.* 2017, 13(2):e1006224.
5. Wang, L.; Huang, H.; Nguyen, H. H.; Allen, K. N.; Mariano, P. S.; Dunaway-Mariano, D. *Biochemistry*, 2010, 49, 1072-1081.
6. Inuke, S.; Aiba, T.; Kawakami, S.; Akiyama, T.; Inoue, J.; Fujimoto, Y. *Org. Lett.*, 2017, DOI: 10.1021/acs.orglett.7b01158.
7. Rosenfeld, D. A.; Richtmyer, N. K.; Hudson, C. S. *J. Am. Chem. Soc.*, 1951, 73, 4907-4910.
8. Hulyalkar, R. K.; Jones, J. K. N.; Perry, M. B. *Can. J. Chem.*, 1963, 41, 1490-1492.
9. Brimacombe, J. S.; Kabir, A. K. M. S. *Carbohydr. Res.*, 1986, 152, 329-334.
10. Brimacombe, J. S.; Kabir, A. K. M. S. *Carbohydr. Res.*, 1986, 150, 35-51.
11. Guzleck, H.; Graziani, A.; Kosma, P. *Carbohydr. Res.*, 2005, 340, 2808-2811.
12. Durka, M.; Tikad, A.; Perion, R.; Bosco, M.; Andaloussi, M.; Floquet, S.; Malacain, E.; Moreau, F.; Oxoby, M.; Gerusz, V.; Vincent, S. P. *Chem. Eur. J.* 2011, 17, 11305-11313.
13. Zamyatina, A.; Gronow, S.; Puchberger, M.; Graziani, A.; Hofinger, A.; Kosma, P. *Carbohydr. Res.*, 2003, 338, 2571-2589.
14. Sabesan, S.; Neira, S. *Carbohydr. Res.* 1992, 223, 169-185.
15. Crich, D.; Dudkin, V. *Org. Lett.*, 2000, 2, 3941-3943.
16. Li, T.; Tikad, A.; Pan, W.; Vincent, S. P. *Org. Lett.*, 2014, 16, 5628-5631.
17. Gaudet, R. G.; Guo, C. X.; Molinaro, R.; Kottwitz, H.; Rohde, J. R.; Dangeard, A.-S.; Arrieumerlou, C.; Girardin, S. E.; Gray-Owen, S. D. *Cell Rep.*, 2017, 19, 1418-1430.
18. Sauvageau et al., *Carbohydr. Res.*, 2017, 450, 38-43.
19. Adekoya et al. *J. Immunol.*, 2018, doi:10.4049/jimmunol.1801012.
20 Zhou et al. *Nature*, 2018, 561, 123-126.

The invention claimed is:

1. A compound of formula (I):

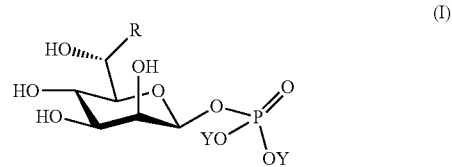

wherein
Y is H or an atom for forming a salt thereof; and
R is a moiety for conjugating to a functional molecule, and
R is selected from the group consisting of: —$C_{1-6}$ alkyl-O—$C_{1-6}$ alkyl-$NH_2$, —$C_{1-6}$ alkyl-$NH_2$, —C(O)OH, —C(O)H, —$C_{0-6}$ alkyl-C(O)$C_{0-6}$ alkyl-$NH_2$, and —$C_{1-6}$ alkyl-$N_3$.

2. The compound of claim 1, wherein Y is Na or H.

3. The compound of claim 1, wherein R is selected from the group consisting of: —$CH_2$—O—$C_{2-4}$ alkyl-$NH_2$, —$C_{1-4}$ alkyl-$NH_2$, —C(O)OH, —C(O)H, —C(O)$C_{0-3}$ alkyl-$NH_2$, and —$C_{1-3}$ alkyl-$N_3$.

4. The compound of claim 1, wherein R is selected from the group consisting of: —$CH_2$—O—$CH_2CH_2$-$NH_2$, —$CH_2$-$NH_2$; —C(O)OH, —C(O)H, —C(O)$NH_2$, and —$CH_2N_3$.

5. The compound of claim 1, selected from the group consisting of:

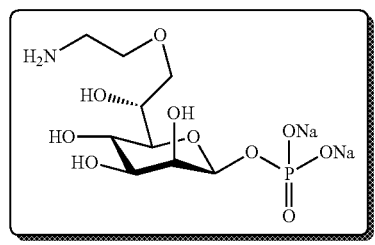

JS10a

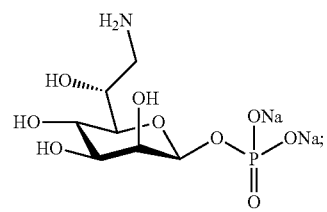

JS15

-continued

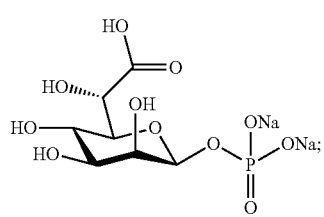
JS16

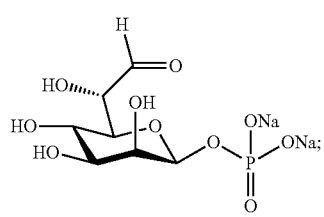
JS17

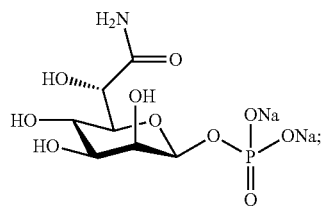
JS18

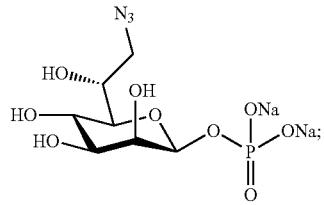
JS19 and the corresponding dihydrogen phosphate thereof.

6. A compound comprising a functional molecule conjugated to a compound of formula (I) as defined in claim 1, wherein the functional molecule is conjugated via the R group of the compound of formula (I), and wherein the functional molecule is an anti-HIV drug.

7. The compound of claim 6, wherein the anti-HIV drug is selected from the group consisting of: a Nucleoside/Nucleotide reverse transcriptase inhibitors (NRTI), a Non-nucleoside reverse transcriptase inhibitor (NNRTI), a protease inhibitor (PI), an Entry inhibitor, a Chemokine co-receptor antagonist (CCR5 antagonist), an integrase inhibitor, and a Cytochrome P4503A (CYP3A) inhibitor.

8. The compound of claim 7, wherein:
the Nucleoside/Nucleotide reverse transcriptase inhibitor (NRTI) is selected from the group consisting of: abacavir (ziagen), emtriacitabine (emtriva), lamivudine (Epivir), zidovudine (Retrovir), didanosine, tenofovir disoproxil fumarate (Viread), and stavudine (Zerit);

the Non-nucleoside reverse transcriptase inhibitor (NNRTI) drug is selected from the group consisting of: rilpivirine (Edurant), etravirine (Intelence), delavirdine mesylate (Rescriptor), efavirenz (Sustiva), and nevirapine;

the protease inhibitor (PI) drug is selected from the group consisting of: tipranavir (Aptivus), indinavir (Crixivan), saquinavir (Invirase), fosamprenavir (Lexiva), ritonavir (Norvir), darunavir (Prezista), atazanavir (Reyataz) and nelfinavir (Viracept);

the entry inhibitor drug is enfuvirtide (Fuzeon);

the integrase inhibitor drug is selected from the group consisting of: raltegravir (Isentress), dolutegravir (Tivicay) and elvitegravir (Vitekta); or the chemokine co-receptor (CCR5) antagonist is maraviroc (Selzentry).

9. A method for the treatment of HIV comprising administering to a subject an effective amount of the compound of claim 6.

10. The compound of claim 1 having the following structural formula:

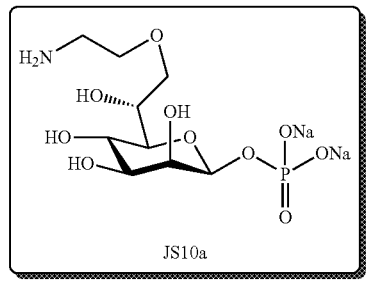
JS10a or the corresponding dihydrogen phosphate thereof.

11. The compound of claim 6 having the following structural formula:

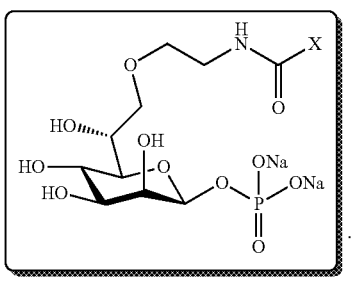
IIa or the corresponding dihydrogen phosphate thereof, wherein X is an anti-HIV drug.

12. A compound selected from the group consisting of:
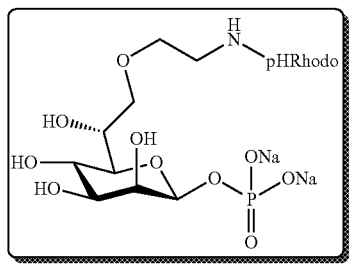
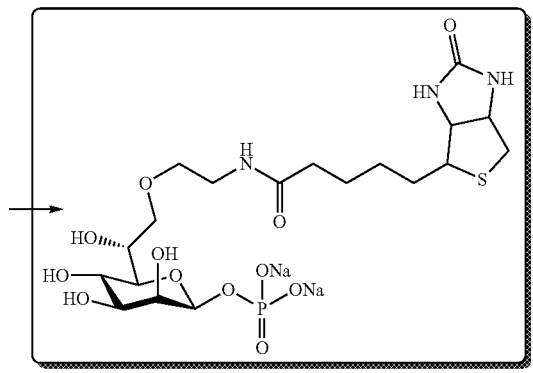
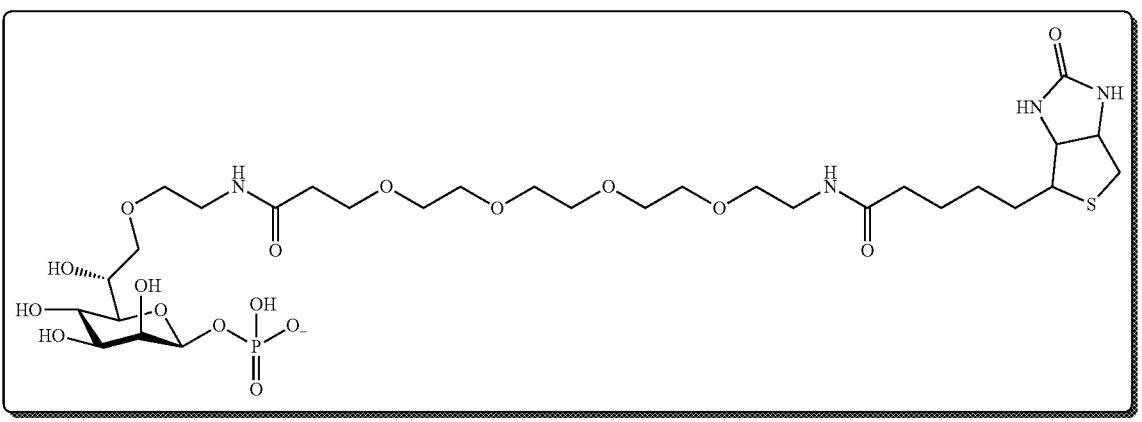
; and
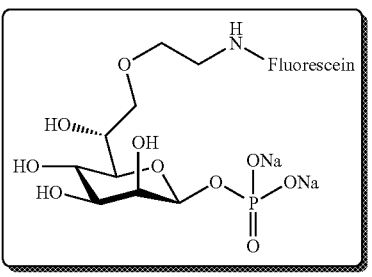
.
* * * * *